US012686855B2

(12) United States Patent
Petersen et al.

(10) Patent No.: US 12,686,855 B2
(45) Date of Patent: Jul. 21, 2026

(54) GENERATION OF PANCREATIC ENDODERM FROM STEM CELL DERIVED DEFINITIVE ENDODERM

(71) Applicant: ASPECT BIOSYSTEMS LTD., Vancouver (CA)

(72) Inventors: Dorthe Roenn Petersen, Slangerup (DK); Christian Honore, Vanloese (DK)

(73) Assignee: ASPECT BIOSYSTEMS LTD., Vancouver (CA)

( * ) Notice: Subject to any disclaimer, the term of this patent is extended or adjusted under 35 U.S.C. 154(b) by 972 days.

(21) Appl. No.: 17/602,177

(22) PCT Filed: Apr. 7, 2020

(86) PCT No.: PCT/EP2020/059842
§ 371 (c)(1),
(2) Date: Oct. 7, 2021

(87) PCT Pub. No.: WO2020/207998
PCT Pub. Date: Oct. 15, 2020

(65) Prior Publication Data
US 2022/0177849 A1 Jun. 9, 2022

(30) Foreign Application Priority Data
Apr. 8, 2019 (EP) .................................... 19167800

(51) Int. Cl.
*C12N 5/071* (2010.01)
*A61K 35/39* (2015.01)

(52) U.S. Cl.
CPC ........... *C12N 5/0676* (2013.01); *A61K 35/39* (2013.01); *C12N 2501/10* (2013.01); *C12N 2501/115* (2013.01); *C12N 2501/155* (2013.01); *C12N 2501/385* (2013.01); *C12N 2501/727* (2013.01); *C12N 2506/45* (2013.01)

(58) Field of Classification Search
CPC .............. C12N 5/0676; C12N 2501/10; C12N 2501/115; C12N 2501/155; C12N 2501/385; C12N 2501/727; C12N 2506/45; A61K 35/39
See application file for complete search history.

(56) References Cited

U.S. PATENT DOCUMENTS

| 10,030,229 B2 | 7/2018 | Peterson et al. |
|---|---|---|
| 10,221,392 B2 | 3/2019 | Ekberg et al. |
| 10,752,884 B2 | 8/2020 | Han et al. |
| 2005/0009868 A1 | 1/2005 | Underhill et al. |
| 2007/0259423 A1 | 11/2007 | Odorico et al. |
| 2009/0263896 A1 | 10/2009 | Kelly et al. |
| 2009/0325294 A1 | 12/2009 | Nelson |
| 2010/0028307 A1 | 2/2010 | O'Neil |
| 2010/0112691 A1 | 5/2010 | Green et al. |
| 2011/0151560 A1 | 6/2011 | Xu |
| 2011/0281355 A1 | 11/2011 | Xu |
| 2013/0031645 A1 | 1/2013 | Touboul et al. |
| 2014/0186953 A1 | 7/2014 | Rezania |
| 2014/0329321 A1* | 11/2014 | Rajesh ................. C12N 5/0676 435/377 |
| 2015/0225698 A1 | 8/2015 | Vallier et al. |
| 2016/0215268 A1 | 7/2016 | Fryer et al. |
| 2016/0326495 A1 | 11/2016 | Ekberg et al. |
| 2018/0087034 A1 | 3/2018 | Hebrok et al. |
| 2018/0216076 A1 | 8/2018 | Hebrok et al. |
| 2018/0327719 A1 | 11/2018 | Osafune et al. |

FOREIGN PATENT DOCUMENTS

| CN | 104755607 A | 7/2015 |
|---|---|---|
| CN | 105579577 A | 5/2016 |
| CN | 106414718 A | 2/2017 |
| CN | 107429225 A | 12/2017 |
| EP | 1786896 | 5/2007 |
| EP | 2505639 A1 | 12/2009 |
| EP | 2233566 A1 | 9/2010 |
| EP | 3031905 A1 | 6/2016 |
| JP | 2013526279 A | 6/2013 |
| JP | 2017537649 A | 12/2017 |
| JP | 6470687 B2 | 2/2019 |
| WO | 03029445 A1 | 4/2003 |

(Continued)

OTHER PUBLICATIONS

Rezania, Alireza, et al. "Enrichment of human embryonic stem cell-derived NKX6. 1-expressing pancreatic progenitor cells accelerates the maturation of insulin-secreting cells in vivo." Stem cells 31.11 (2013): 2432-2442. (Year: 2013).*

Memon, Bushra, et al. "Enhanced differentiation of human pluripotent stem cells into pancreatic progenitors co-expressing PDX1 and NKX6. 1." Stem cell research & therapy 9 (2018): 1-15. (Year: 2018).*

Pagliuca, Felicia W., et al. "Generation of functional human pancreatic β cells in vitro." Cell 159.2 (2014): 428-439. (Year: 2014).*

Rezania, Alireza, et al. "Reversal of diabetes with insulin-producing cells derived in vitro from human pluripotent stem cells." Nature biotechnology 32.11 (2014): 1121-1133. (Year: 2014).*

Stafford, David, and Victoria E. Prince. "Retinoic acid signaling is required for a critical early step in zebrafish pancreatic development." Current Biology 12.14 (2002): 1215-1220. (Year: 2002).*

(Continued)

*Primary Examiner* — Teresa E Knight
*Assistant Examiner* — Michael Angelo Riga
(74) *Attorney, Agent, or Firm* — Todd Lorenz

(57) ABSTRACT

The present invention relates to methods of efficiently generating pancreatic endoderm from human pluripotent stem (PS) cell derived human definitive endoderm. The present invention also relates to pancreatic endoderm cells obtained by the methods of the invention. Finally, the present invention relates to culture medium and composition comprising a RAR antagonist and uses of said RAR antagonist in the induction of pancreatic endoderm cells. The present invention provides a more homogenous and synchronised pancreatic cell population, with increased efficiency.

11 Claims, 10 Drawing Sheets

(56) References Cited

FOREIGN PATENT DOCUMENTS

| WO | 03068357 A2 | 8/2003 |
|----|----|----|
| WO | 2005005608 A2 | 1/2005 |
| WO | 2005086860 A2 | 9/2005 |
| WO | 2006134017 A2 | 12/2006 |
| WO | 2007/103282 A2 | 9/2007 |
| WO | 2007127927 A2 | 11/2007 |
| WO | 2008036447 A2 | 3/2008 |
| WO | 2008048671 A1 | 4/2008 |
| WO | 09012428 A2 | 1/2009 |
| WO | 2009006399 A1 | 1/2009 |
| WO | 2009018453 A1 | 2/2009 |
| WO | 2009048675 A1 | 4/2009 |
| WO | 2009096902 A1 | 8/2009 |
| WO | 2009131568 A1 | 10/2009 |
| WO | 2009132063 A2 | 10/2009 |
| WO | 2009132083 A2 | 10/2009 |
| WO | 2010002846 A1 | 1/2010 |
| WO | 2010051213 A1 | 5/2010 |
| WO | 2010051223 A1 | 5/2010 |
| WO | 2010053472 A1 | 5/2010 |
| WO | 2010057039 A2 | 5/2010 |
| WO | 2010059775 A1 | 5/2010 |
| WO | 2010091241 A2 | 8/2010 |
| WO | 2010124142 A2 | 10/2010 |
| WO | 2010136583 A2 | 12/2010 |
| WO | 2011011302 A2 | 1/2011 |
| WO | 2011011349 A2 | 1/2011 |
| WO | 2011079017 A2 | 6/2011 |
| WO | 2011079018 A2 | 6/2011 |
| WO | 2011081222 | 7/2011 |
| WO | 2011100291 A1 | 8/2011 |
| WO | 11143299 A2 | 11/2011 |
| WO | 2012025914 A1 | 3/2012 |
| WO | 2012030540 A2 | 3/2012 |
| WO | 2012175633 A1 | 12/2012 |
| WO | 13095953 | 6/2013 |
| WO | 2014033322 A1 | 3/2014 |
| WO | 2018138281 A1 | 8/2018 |

OTHER PUBLICATIONS

Alvarez, Susana, et al. "Retinoic acid receptor modulators: a perspective on recent advances and promises." Expert opinion on therapeutic patents 21.1 (2011): 55-63. (Year: 2011).*

Bayha et al., "Retinoic Acid Signaling Organizes Endodermal Organ Specification along the Entire Antero-Posterior Axis." PloS ONE, 2009, vol. 4, No. 6, e5845, pp. 1-15.

Brun et al., "Retinoic acid receptor signaling is required to maintain glucose-stimulated insulin secretion and ?-cell mass." The FASEB Journal, 2015, vol. 29, No. 2, pp. 671-683.

Johannesson et al., "FGF4 and retinoic acid direct differentiation of hESCs into PDX1-expressing foregut endoderm in a time and concentration-dependent manner." PloS one, 2009, vol. 4, No. 3, e4794, p. 1-13.

Rezania et al., "Reversal of diabetes with insulin-producing cells derived in vitro from human pluripotent stem cells." Nature Biotechnology, 2014, vol. 32, No. 11, pp. 1121-1133.

Schneider et al., "Local retinoid signaling coordinates forebrain and facial morphogenesis by maintaining FGF8 and SHH." Development, 2001, vol. 128, No. 14, pp. 2755-2767.

Soprano et al., "Role of Retinoic Acid in the Differentiation of Embryonal Carcinoma and Embryonic Stem Cells." Stem Cell Regulators; IN: Vitamins and hormones : advances in research and applications, 2007, vol. 75, pp. 69-95.

Mfopou J K et al., Noggin, Retinoids, and Fibroblast Growth Factor Regulate Hepatic or Pancreatic Fate of Human Embryonic Stem Cells, Journal: Gastroenterology, vol. 138, Year: 2010, pp. 2233-2245.

Leon-Quinto T et al, In vitro directed differentiation of mouse embryonic stem cells into insulin-producing cells, Journal: Diabetologia, vol. 47, Year: 2004, pp. 1442-1451.

Shiraki N et al., Guided Differentiation of Embryonic Stem Cells into Pdx1-Expressing Regional-Specific Definitive Endoderm, Journal: Stem Cells, vol. 26, Year: 2008, pp. 874-885.

Zhang D et al, Highly efficient differentiation of human ES cells and iPS cells into mature pancreatic insulin-producing cells, Journal: Cell Research, vol. 19, Year: 2009, pp. 429-438.

Chen S et al., A small molecule that directs differentiation of human ESCs into the pancreatic lineage, Journal: Nature Chemical Biology, vol. 5, No. 4, Year: 2009, pp. 258-265.

Surmacz B et al., Directing Differentiation of Human Embryonic Stem Cells Toward Anterior Neural Ectoderm Using Small Molecules, Journal: Stem Cells, vol. 30, No. 9, Year: 2012, pp. 1875-1884.

Charton J et al., Novel non-carboxylic acid retinoids: 1,2,4-Oxadiazol-5-one derivatives, Journal: Bioorganic & Medicinal Chemistry Letters, vol. 19, No. 2, Year: 2009, pp. 489-492.

Nostro M C et al., Stage-specific signaling through TGF[beta] family members and WNT regulates patterning and pancreatic specification of human pluripotent stem cells, Journal: Development, vol. 138, No. 5, Year: 2011, pp. 861-871.

Cuny G D et al., Structure-activity relationship study of bone morphogenetic protein (BMP) signaling inhibitors, Journal: Bioorganic & Medicinal Chemistry Letters, vol. 18, No. 15, Year: 2008, pp. 4388-4392.

Kroon E et al., Pancreatic endoderm derived from human embryonic stem cells generates glucose-responsive insulin-secreting cells in vivo. Journal: Nature Biotechnology, vol. 26, No. 4, pp. 443-452.

D'Amour et al., Production of pancreatic hormone-expressing endocrine cells from human embryonic stem cells, Journal: Nature Biotechnology, vol. 24, No. 11, Year: 2006, pp. 1392-1401.

Cai J et al., Generation of Homogeneous PDX1φ Pancreatic Progenitors from Human ES Cell-derived Endoderm Cells, Journal: Journal of Molecular Cell Biology, Year: 2010, vol. 2, pp. 50-60.

Ameri J et al., FGF2 Specifies hESC-Derived Definitive Endoderm into Foregut/Midgut Cell Lineages in a Concentration-Dependent Manner, Journal: Stem Cells, vol. 28, Year 2010, pp. 45-56.

Kunisada Y et al., Small molecules induce efficient differentiation into insulin-producing cells from human induced pluripotent stem cells, Journal: Stem Cell Research, vol. 8, Year: 2012, pp. 274-284.

Schulz T C et al., A Scalable System for Production of Functional Pancreatic Progenitors from Human Embryonic Stem Cells, Journal: PLoS One, vol. 7, No. 5, Year: 2012, pp. 1-17.

Kim et al. "Signaling and Transcriptional Control of Pancreatic Organogenesis." Current Opinion in Genetics and Development 2002 vol. 12 pp. 540-547.

Millipore Sigma, "JNK Inhibitor II—CAS 129-56-6—Calbiochem", Data Sheet, Jun. 8, 2009, 4 pages, accessed Oct. 8, 2021: https://www.emdmillipore.com/US/en/product/JNK-Inhibitor-II-CAS-129-56-6-Calbiochem,EMD_BIO-420119?bd=1#anchor_PDS.

Alvarez et al., "Retinoic acid receptor modulators: a perspective on recent advances and promises", Expert Opinion on Therapeutic Patents, Nov. 20, 2010, vol. 21, No. 1, pp. 55-63.

Hopkins, "Inhibitors of the bone morphogenetic protein (BMP) signaling pathway: a patent review (2008-2015)", Expert Opinion on Therapeutic Patents, Aug. 4, 2016, vol. 26, No. 10, pp. 1115-1128.

Cai et al., "Generation of homogeneous PDX1(+) pancreatic progenitors from human ES cell-derived endoderm cells", Journal of Molecular Cell Biology, Nov. 2009, vol. 2, pp. 50-60.

* cited by examiner

Standard

AGN193109

10μM AGN PE2-3

GENERATION OF PANCREATIC ENDODERM FROM STEM CELL DERIVED DEFINITIVE ENDODERM

CROSS-REFERENCE TO RELATED APPLICATIONS

This application is a 35 U.S.C. § 371 National Stage application of International Application PCT/EP2020/059842 (WO 2020/207998), filed Apr. 7, 2020, which claims priority to European Patent Application 19167800.2, filed Apr. 8, 2019; the contents of which are incorporated herein by reference.

TECHNICAL FIELD

The present invention relates to methods of efficiently generating pancreatic endoderm from human pluripotent stem (PS) cell derived human definitive endoderm.

BACKGROUND

Beta cell (BC) transplantation potentially provides the ultimate cure for type I diabetes. However, the limited availability of donor beta cells constrains the use of this treatment as a clinical therapy. Pluripotent stem (PS) cells can proliferate infinitely and differentiate into many cell types. Thus, PS cells are a promising source for beta cells, but before PS cells can be used to treat diabetes, they need to be efficiently and reproducibly differentiated to pancreatic cells.

During vertebrate embryonic development, a pluripotent cell gives rise to the three germ layers: ectoderm, mesoderm and endoderm. Induction of definitive endoderm (DE) is the first step towards formation of endoderm derived tissues. Generation of pancreatic endoderm (PE) from DE cells is necessary for the generation of insulin-producing beta cells. PE cells with the potential to become endocrine progenitors (EP) are characterized by co-expression of two important transcription factors, PDX1 and NKX6.1.

Stepwise in vitro differentiation protocols have been established for generating pancreatic cells from PS cells. These protocols generally mimic the major events of pancreatic development, which includes several stages such as formation of the DE which co-expresses SOX17 and FOXA2, primitive gut, posterior foregut, PE, EP and ultimately the mature beta cells. To date, efficient DE differentiation of hES cells has been achieved by activin A treatment. The next major step in generating pancreatic beta cells is to generate PE that co-expresses PDX1 and NKX6.1. Several groups have developed in vitro protocols that can differentiate PS cells into DE and PE and almost all published protocols include a step of adding retinoic acid receptor (RAR) agonist in the induction of PE.

Patients with type 1 diabetes can be treated with transplantation of pancreatic islets from human donors and some patients achieve insulin independence. However, donor islets are scarce and of variable quality, and insulin producing cells derived from pluripotent stem cells offer an attractive alternative to pancreatic islets. A key differentiation step is the differentiation to pancreatic endoderm (PE) from definitive endoderm (DE), characterized by the co-expression of PDX1 and NKX6.1, but is less efficient than the previous differentiation step to DE and one where batch to batch variation is often observed. An increase in the efficiency of PE induction would increase the number of endocrine progenitors (EP) able to form beta cells and also reduce the number of unwanted cell types. Variation in differentiation efficiency from batch to batch is a well-known problem and improving differentiation stability will be important as we move towards large scale production processes and clinical trials. Differentiation protocols must be therefore optimised at all stages to yield functional beta cells (BCs) in high numbers at the final step. Thus, there is a need to increase efficiency and stability of the current differentiation protocols, which is important for the further development of these cells towards the endocrine lineage.

SUMMARY

The present invention improves the efficiency of differentiating human PS cells towards mature beta cells, by providing a method to increase the proportion of NKX6.1/PDX1 double positive cells, a hallmark for PE cells committed to a pancreatic fate.

Furthermore, the present invention provides a more efficient, more homogenous and synchronised pancreatic cell population, which is important for the further development of these cells towards the endocrine lineage.

In one aspect, the invention relates to methods for inducing pancreatic endoderm cells from human pluripotent stem (PS) cell derived human definitive endoderm.

In one aspect, the invention relates to methods for inducing pancreatic endoderm precursor cells from human pluripotent stem (PS) cell derived human definitive endoderm, wherein said methods comprise a step of culturing the definitive endoderm with a RAR antagonist.

In one aspect, the invention relates to methods for inducing pancreatic endoderm cells from human pluripotent stem (PS) cell derived human definitive endoderm, wherein said methods comprise a step of culturing the definitive endoderm with a RAR antagonist to obtain pancreatic endoderm precursors followed by induction of pancreatic endoderm cells by culturing the pancreatic endoderm precursors with a RAR agonist.

In one aspect, the invention relates to a method of differentiating definitive endoderm cells derived from human pluripotent stem cells into pancreatic endoderm precursors comprising a step of culturing definitive endoderm (DE) in a culture medium comprising a retinoic acid receptor (RAR) antagonist.

In one aspect, the invention further comprises a step of culturing the pancreatic endoderm precursors in a cell culture medium comprising an RAR agonist, thereby inducing pancreatic endoderm (PE), wherein said cells are PDX1+/NKX6.1+ double positive.

In one aspect, the invention relates to pancreatic endoderm cells or pancreatic endoderm cell precursors obtainable by the methods of the present invention.

In another aspect, the invention relates to synchronized pancreatic endoderm cells or synchronized pancreatic endoderm cell precursors obtainable by the methods of the present invention.

In one aspect, the invention relates to a culture medium and or composition comprising a RAR antagonist and a RAR agonist.

In one aspect, the invention relates to a pancreatic endoderm cell produced by exposing a definitive endoderm derived from human pluripotent stem cell to a RAR antagonist to obtain a pancreatic endoderm precursor, followed by exposure of the pancreatic endoderm precursor to a RAR agonist to obtain pancreatic endoderm.

In one aspect, the invention relates to use of a RAR antagonist, to induce pancreatic endoderm precursors from definitive endoderm cell derived from human pluripotent stem cells.

In one aspect, the invention relates to use of a RAR antagonist, followed by use of a RAR agonist, to induce pancreatic endoderm cells from definitive endoderm cells derived from human pluripotent stem cells.

In one aspect, the invention relates to a bioreactor comprising pancreatic endoderm precursor cell or pancreatic endoderm cell populations obtained by the methods of the present invention.

In one aspect, the invention provides an improved pancreatic endoderm cell population, i.e. PE with increased fraction of NKX6.1+/PDX1+ double positive cells.

In one aspect, the present invention provides a more homogenous pancreatic endoderm cell population.

In one aspect, the present invention provides a more synchronised pancreatic endoderm cell population.

The present invention may also solve further problems that will be apparent from the disclosure of the exemplary embodiments.

BRIEF DESCRIPTION OF DRAWINGS

FIG. 2A shows the effect on the expression of pancreatic endoderm markers Nkx6.1, CPA1, Ptf1a and Dlk1 on PE10 of inhibition of RA signalling by AGN193109 or activation of RA signalling by AM580 on PE2-3, evaluated by Nanostring analysis of gene expression. FIG. 2B shows a FACS plot of the expression of Dlk1 relative to Nkx6.1 on PE11 in the standard protocol compared to the AGN 193109 treatment.

FIG. 3A shows the effect of inhibition of RA signalling by AGN193109 and activation of RA signalling by AM580 on PE2-3 on pancreatic endocrine markers NeuroD and Ngn3 at the pancreatic endoderm stage, compared to the standard protocol, evaluated by Nanostring analysis of gene expression. FIG. 3B shows a FACS plot of the expression of the pancreatic endocrine marker Nkx2.2 on PE10 in the standard protocol compared to AGN 193109 treatment on PE2-3.

FIG. 7A shows an average of the percentage of C-pep/Nkx6.1 double positive cells in 4 independent experiments comparing the standard protocol to AGN 193109 treatment on PE2-3. FIG. 7B shows a representative example comparing the standard protocol to AGN 193109 treatment.

DESCRIPTION

Figure 1A:
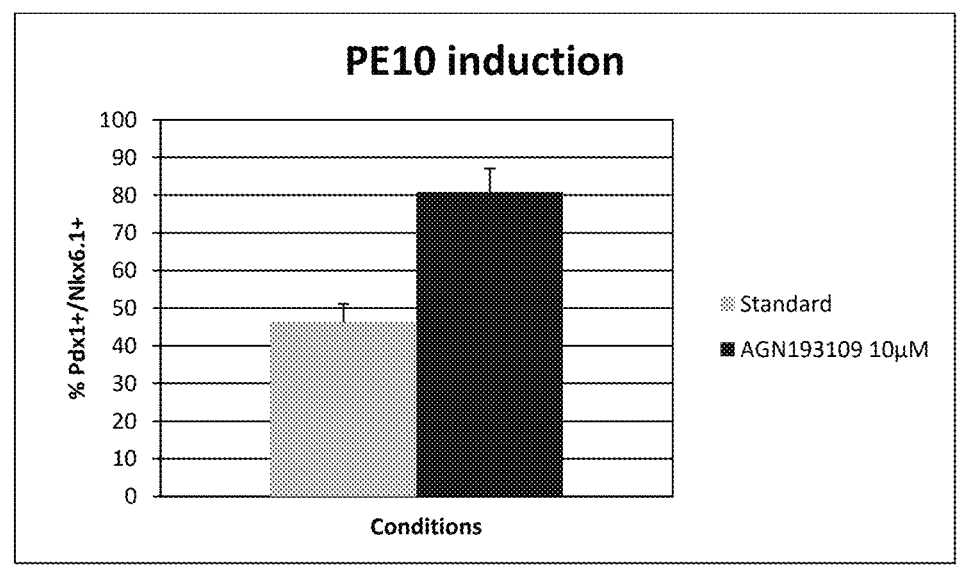
FIGS. 1A-C show the effect of AGN 193109 compared to standard PE induction protocol evaluated by FACS analysis on Pdx1/Nkx6.1 expression on day 10 of PE differentiation (PE10). The figure shows an average of the percentage of Pdx1/Nkx6.1 double positive cells in 4 independent experiments comparing the standard PE to the AGN 193109 treatment (FIG. 1A) as well as one example of a FACS plot from a representative experiment (FIG. 1B). In addition, we show an example of the effect of AGN193109 on PE10 induction when applied to a suboptimal induction using the standard protocol (FIG. 1C).
Figure 1B:
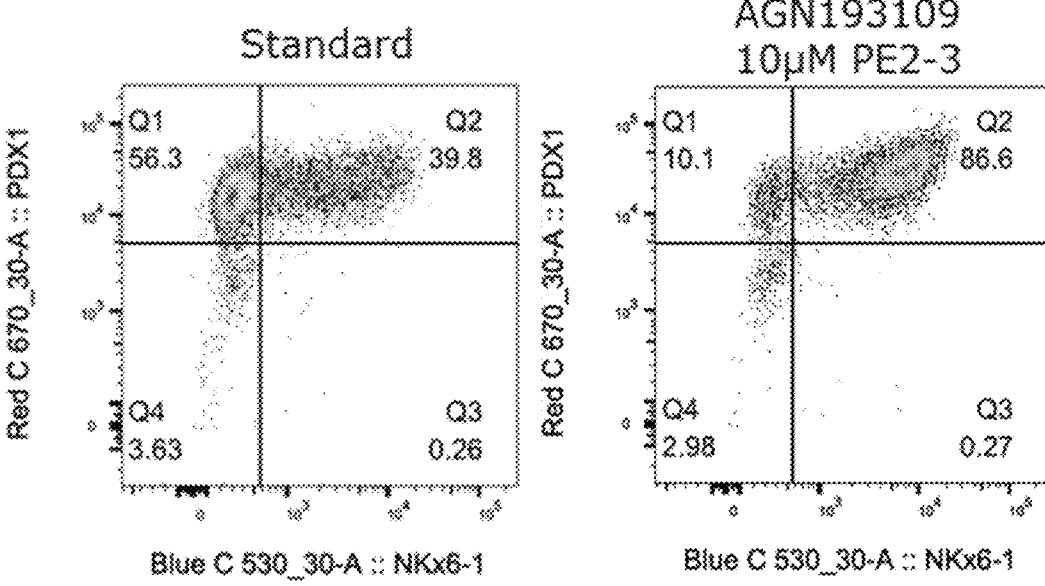
Figure 1C:
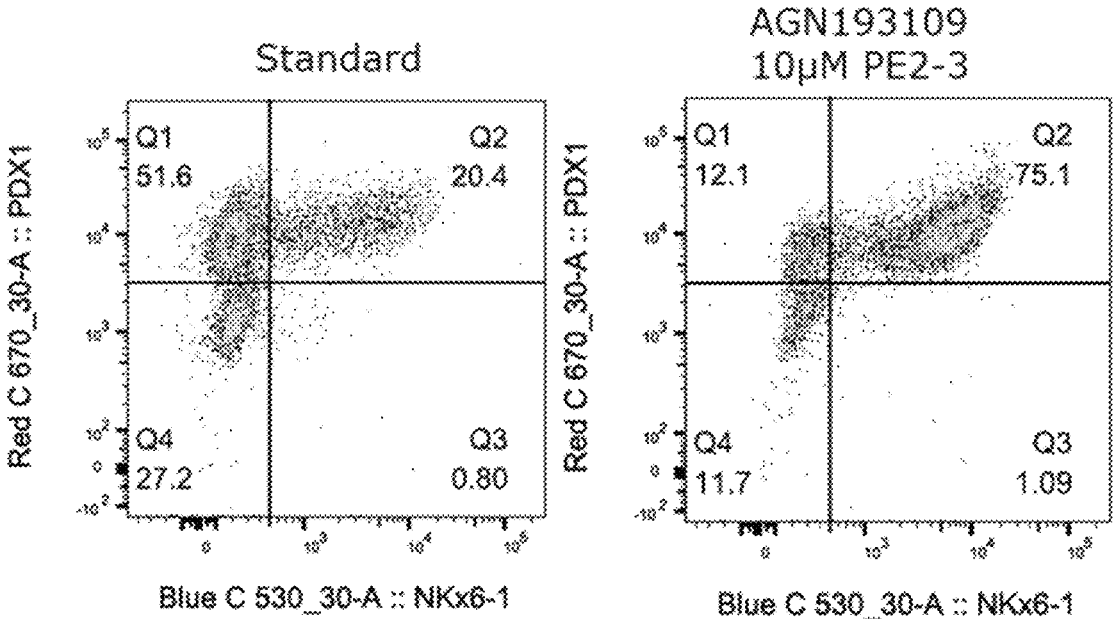

The present invention relates to methods of generating pancreatic endoderm precursors and pancreatic endoderm from definitive endoderm derived from human pluripotent stem cells.

The present invention relates to methods of differentiating definitive endoderm cells derived from human pluripotent stem cells into pancreatic endoderm NKX6.1+/PDX1+ double positive, comprising a step of culturing definitive endoderm in a culture medium comprising a retinoic acid receptor (RAR) antagonist to obtain pancreatic endoderm precursors, followed by a step of culturing the pancreatic endoderm precursors in a culture medium comprising a retinoic acid-receptor agonist.

The present invention provides a more homogenous and synchronised pancreatic endoderm cell population, with increased efficiency.

Transcription factors NKX6.1 and PDX1, are markers of PE cell population, one of the cell stages necessary to reach endocrine cell populations. Increasing the proportion of NKX6.1/PDX1 double positive cells in the PE cell population increases the efficiency.

The differentiation method of the present invention provides a markedly increased proportion of NKX6.1/PDX1+ double positive cells on PE cell population, i.e. with higher efficiency.

Furthermore, the present invention provides a more homogenous and synchronised pancreatic endoderm cell population, which is important for the further development of these cells towards the endocrine lineage, i.e., into beta cells or insulin producing cells.

In the present invention, we describe a method to increase efficiency and stability of PE induction, which also improves the efficiency of the further differentiation into insulin producing beta cells.

By including a retinoic acid receptor (RAR) antagonist (AGN 193109) during the first stage of the PE protocol (the LDN stage i.e. 4 days referred to as PE0-PE3) we can significantly increase PE induction in the second stage (i.e. 8 days referred to as PE4-PE11) containing a retinoic acid receptor agonist (percentage of PDX1+/NKX6.1+ pancreatic endoderm). Furthermore, we reduce variation from batch to batch and stabilize PE induction. Finally, the quality of the pancreatic endoderm is improved since the expression of Ptf1a, an additional marker of PE, is increased.

In the present invention we also describe DLK1 as a marker of pancreatic endoderm and show that DLK1 is primarily expressed in PDX1+/NKX6.1-high cells. DLK1 is a surface marker and can be used for the enrichment of pancreatic endoderm at the pancreatic endoderm stage, by live cell sorting using methods such as FACS or MACS.

PE cells can differentiate into EP cells that can further differentiate into BC cells. Finally, the improvement in the PE step leads to an overall improvement in BC differentiation efficiency, yielding a higher number of C-pep/NKX6.1 double positive cells.

Definitions

Stem Cells

Stem cells are undifferentiated cells defined by their ability at the single cell level to both self-renew and differentiate to produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts.

Stem cells are classified by their developmental potential as: (1) totipotent, meaning able to give rise to all embryonic and extraembryonic cell types; (2) pluripotent, meaning able to give rise to all embryonic cell types; (3) multi-potent, meaning able to give rise to a subset of cell lineages, but all within a particular tissue, organ, or physiological system (for example, hematopoietic stem cells (HSC) can produce progeny that include HSC (self-renewal), blood cell restricted oligopotent progenitors and all cell types and elements (e.g., platelets) that are normal components of the blood); (4) oligopotent, meaning able to give rise to a more restricted subset of cell lineages than multi-potent stem cells; and (5) unipotent, meaning able to give rise to a single cell lineage (e.g., spermatogenic stem cells).

Human Pluripotent Stem Cells

As used herein, "human pluripotent stem cells" (hPSC) refers to cells that may be derived from any source and that are capable, under appropriate conditions, of producing human progeny of different cell types that are derivatives of all the 3 germinal layers (endoderm, mesoderm, and ectoderm). hPSC may have the ability to form a teratoma in 8-12 week old SCID mice and/or the ability to form identifiable cells of all three germ layers in tissue culture. Included in the definition of human pluripotent stem cells are embryonic cells of various types including human blastocyst derived stem (hBS) cells in literature often denoted as human embryonic stem (hES) cells, (see, e.g., Thomson et al. (1998), Heins et al. (2004), as well as induced pluripotent stem cells (see, e.g. Yu et al. (2007); Takahashi et al. (2007)). The various methods and other embodiments described herein may require or utilise hPSC from a variety of sources. For example, hPSC suitable for use may be obtained from developing embryos. Additionally, or alternatively, suitable hPSC may be obtained from established cell lines and/or human induced pluripotent stem (hiPS) cells.

As used herein "hiPSC" refers to human induced pluripotent stem cells.

ES cell lines can also be derived from single blastomeres without the destruction of ex utero embryos and without affecting the clinical outcome (Chung et al. (2006) and Klimanskaya et al. (2006)).

Blastocyst-Derived Stem Cell

As used herein, the term "blastocyst-derived stem cell" is denoted BS cell, and the human form is termed "hBS cells". In literature the cells are often referred to as embryonic stem cells, and more specifically human embryonic stem cells (hESC). The pluripotent stem cells used in the present invention can thus be embryonic stem cells prepared from blastocysts, as described in e.g. WO 03/055992 and WO 2007/042225, or be commercially available hBS cells or cell lines. However, it is further envisaged that any human pluripotent stem cell can be used in the present invention, including differentiated adult cells which are reprogrammed to pluripotent cells by e.g. treating adult cells with certain transcription factors, such as OCT4, SOX2, NANOG, and LIN28 as disclosed in Yu, et al. (2007); Takahashi et al. (2007) and Yu et al. (2009).

In one embodiment, the cell population comprising PE cells is obtained from a somatic cell population. In another embodiment, the somatic cell population has been induced to de-differentiate into an embryonic-like stem (ES, e.g., a pluripotent) cell. Such de-differentiated cells are also termed induced pluripotent stem cells (iPSC).

In one embodiment, the cell population comprising PE cells is obtained from embryonic stem (ES, e.g., pluripotent) cells. In another embodiment, the cell population comprising pancreatic cells is pluripotent cells such as ES like-cells.

In one embodiment, the cell population comprising PE cells is embryonic differentiated stem (ES or pluripotent) cells. Differentiation takes place in embryoid bodies and/or in monolayer cell cultures or a combination thereof.

In one embodiment, the cell population is a population of stem cells. In another embodiment, the cell population is a population of stem cells differentiated to the pancreatic endoderm lineage.

In one embodiment, the stem cells that are further differentiated are human embryonic stem cells or induced pluripotent stem cells.

Differentiation

As used herein "differentiate" or "differentiation" refers to a process where cells progress from an undifferentiated state to a differentiated state, from an immature state to a less immature state or from an immature state to a mature state. For example, early undifferentiated embryonic pancreatic cells are able to proliferate and express characteristic markers, like PDX1, NKX6.1 and PTF1a. Mature or differentiated pancreatic cells do not proliferate and do secrete high levels of pancreatic endocrine hormones or digestive enzymes. For example, fully differentiated beta cells secrete insulin at high levels in response to glucose. Changes in cell interaction and maturation occur as cells lose markers of undifferentiated cells or gain markers of differentiated cells. Loss or gain of a single marker can indicate that a cell has "matured or fully differentiated."

The term "differentiation factor" refers to a compound added to pancreatic cells to enhance their differentiation to mature endocrine cells also containing insulin producing beta cells.

Exemplary differentiation factors include hepatocyte growth factor, keratinocyte growth factor, exendin-4, basic fibroblast growth factor, insulin-like growth factor-1, nerve growth factor, epidermal growth factor platelet-derived growth factor, and glucagon-like peptide 1.

In one embodiment, differentiation of the cells comprises culturing the cells in a medium comprising one or more differentiation factors.

Definitive Endoderm Cells (DE Cells)

Definitive endoderm cells are characterised by expression of the marker SOX17. Further markers of DE are FOXA2 and CXCR4.

"SOX17" (SRY-box 17) as used herein is a member of the SOX (SRY-related HMG-box) family of transcription factors involved in the regulation of embryonic development and in the determination of the cell fate.

"FOXA2" (forkhead box A2) as used herein is a member of the forkhead class of DNA-binding proteins.

"CXCR4" (C-X-C motif chemokine receptor 4) as used herein is a CXC chemokine receptor specific for stromal cell-derived factor-1.

Non-limiting examples of DE inducing protocols is the conventional D'Amour protocol (Novocell, Nature Biotec 2006, 2008) and the protocol described in WO2012/175633 (which is incorporated herein by reference in its entirety).

In one embodiment, the DE cells of the method of the present invention are SOX17+ positive.

In one embodiment, the DE cells of the method of the present invention are SOX17+/FOXA2 double positive.

In one embodiment, the DE cells of the method of the present invention are SOX17+/FOXA2+/CXCR4+ triple positive.

Pancreatic Endoderm Precursors

As used herein "pancreatic endoderm precursors" or "pancreatic endoderm cell precursors" are the cells obtained from culturing the definitive endoderm cells derived from human pluripotent stem cells in a culture medium comprising a RAR antagonist.

These cells when further cultured in a culture medium comprising a RAR agonist result in induction of pancreatic endoderm cells as defined below.

Pancreatic Endoderm Cells (PE Cells)

Pancreatic endoderm cells are characterised by expression of markers at least 5% NKX6.1+/PDX1+ double positive. Further markers of PE are PTF1A and CPA1.

"PDX1" as used herein, refers to a homeodomain transcription factor implicated in pancreas development.

"NKX6.1" as used herein is a member of the NKX transcription factor family.

"PTF1A" as used herein is a protein that is a component of the pancreas transcription factor 1 complex (PTF1) and is known to have a role in mammalian pancreatic development.

"CPA1" as used herein is a member of the carboxypeptidase A family of zinc metalloproteases. This enzyme is produced in the pancreas.

In one embodiment, the present invention relates to a method of differentiating DE into PE, wherein said cells are NKX6.1+/PDX1+ double positive.

In one embodiment, the present invention relates to a method of differentiating DE into PE, wherein at least 5% of the said PE cells co-express PDX1 and NKX6.1.

In one embodiment, the present invention relates to a method of differentiating DE into PE, wherein at least 5%, at least 10%, 10-30%, 10-40%, 5-70%, 10-80% or 5-100% of the said PE cells are PDX1+/NKX6.1+ double positive.

In one embodiment, the present invention relates to a method of differentiating DE into PE, wherein at least 70% of the said PE cells are PDX1+/NKX6.1+ double positive.

In one embodiment, the present invention relates to a method of differentiating DE into PE, wherein at least 80% of the said PE cells are PDX1+/NKX6.1+ double positive.

In one embodiment, the present invention relates to a method of differentiating DE into PE, wherein at least 90% of the said PE cells are PDX1+/NKX6.1+ double positive.

In one embodiment, the present invention relates to a method of differentiating DE into PE, wherein at least 95% of the said PE cells are PDX1+/NKX6.1+ double positive.

In one embodiment, the present invention relates to a method of differentiating DE into PE, wherein at least 98% of the said PE cells are PDX1+/NKX6.1+ double positive.

In one embodiment, the present invention relates to a method of differentiating DE into PE, wherein 80-100% of the said PE cells are PDX1+/NKX6.1+ double positive.

In one embodiment, the present invention relates to a method of differentiating DE into PE, wherein 90-100% of the said PE cells are PDX1+/NKX6.1+ double positive.

In one embodiment, the present invention relates to in vitro or in vivo pancreatic endoderm cell population obtainable by the methods of the present invention.

In one embodiment, the present invention relates to in vitro pancreatic endoderm cell population obtainable by the methods of the present invention.

In one embodiment, the present invention relates to in vivo pancreatic endoderm cell population obtainable by the methods of the present invention.

In one embodiment, the present invention provides a pancreatic endoderm cell population with increased co-expression of PDX1 and NKX6.1, i.e. with increased expression of PDX1+/NKX6.1+ double positive cells.

In one embodiment, the present invention relates to pancreatic endoderm cell population obtainable by the methods of the present invention, with increased expression of /PDX1+/NKX6.1+ double positive cells.

In one embodiment, the present invention relates to pancreatic endoderm cell population obtainable by the methods of the present invention, wherein said pancreatic endoderm cells are at least 70% PDX1+/NKX6.1+ double positive.

In one embodiment, the present invention relates to pancreatic endoderm cell population obtainable by the methods of the present invention, wherein said pancreatic endoderm cells are 80-100% PDX1+/NKX6.1+ double positive.

In one embodiment, the present invention relates to pancreatic endoderm cell population obtainable by the methods of the present invention, wherein said pancreatic endoderm cells are 90-100% PDX1+/NKX6.1+ double positive.

In one embodiment the present invention provides a method with a shorter LDN stage, reducing the LDN stage.

In one embodiment the present invention provides a method with a shorter LDN stage, reducing the LDN stage to half, i.e., to two days.

In one embodiment, the present invention relates to a method with a shorter duration than the standard method, reducing the LDN stage to two days.

An additional approach to increasing the yield of functional beta cells involves sorting of live cells at some stage during the process of differentiation. Sorting at the pancreatic endoderm stage would be attractive as the wanted cells are committed to the pancreatic lineage at this step. This approach requires the use of antibodies recognizing surface antigens thus allowing for live cells sorting. Here, we describe the discovery of Delta Like Non-Canonical Notch Ligand 1 (DLK1) as a surface marker for human ES cell derived pancreatic endoderm.

A synchronised PE population is one where any premature further differentiation to endocrine progenitors (EP)

does not occur, until the signals for inducing endocrine differentiation is applied to the cell cultures. Premature endocrine differentiation at the PE stage is a common feature of many published protocols. A synchronized PE population is an advantage in that it allows for better control in the induction of the endocrine lineage and beta cells.

Obtaining synchronised cells is an advantage since it leads to more homogeneous cell populations to continue further differentiation, into beta cells or insulin-producing cells.

Transplantation of the differentiated cells at the beta cell stage shows a tendency that addition of AGN193109 improves the beta to alpha cell ratio, meaning that the fraction of insulin positive cells relative to glucagon positive cells is higher with AGN193109 treatment 8 weeks after transplantation, evaluated by immunohistochemistry and quantitative image analysis.

"DLK1" as used herein, is a transmembrane protein that contains multiple epidermal growth factor repeats that functions as a regulator of cell growth. The encoded protein is involved in the differentiation of several cell types. DLK1 is a non-canonical notch ligand.

"NKX2.2" as used herein, is a homeodomain transcription factor. Nkx2.2 is a critical regulator of appropriate islet cell lineage specification during pancreagenesis.

In one embodiment, the present invention provides a PE endoderm cell population that will be induced more selectively, more homogeneously and more efficiently into EP cells and Beta cell populations.

In one embodiment, the pancreatic endoderm cells population obtained by the methods of the present invention are more homogeneous and more synchronised, inducing more efficiently into EP cells and Beta cell populations.

Furthermore, DLK1 is a surface marker that is highly expressed in PE cell populations with improved PDX1/ NKX6.1 expression.

In one embodiment, the PE cells obtainable by the methods of the present invention are DLK1 positive.

In one embodiment, the PE cells obtainable by the methods of the present invention express at least 5% of DLK1.

In one embodiment, the PE cells obtainable by the methods of the present invention express 5-30% of DLK1.

In one embodiment, the present invention relates to a PE cell population, wherein said cells are DLK1 positive.

In one embodiment, the present invention relates to surface marker DLK1 for PE, wherein said cells are NKX6.1+/ PDX1+ double positive.

In one embodiment, the present invention relates to surface marker DLK1 for PE, wherein said cells are about 80% NKX6.1+/PDX1+ double positive.

In one embodiment, the present invention relates to surface marker DLK1 for PE, wherein said cells are more than 80% NKX6.1+/PDX1+ double positive. In one embodiment, the present invention provides improved PE cell populations, with at least 5% expression of DLK1.

In one embodiment, the present invention provides improved PE cell populations, with at least 10% expression of DLK1.

In one embodiment, the present invention provides improved PE cell populations, with at least 20% expression of DLK1.

In one embodiment, the present invention provides improved PE cell populations, with at least 30% expression of DLK1.

In one embodiment, the present invention provides improved PE cell populations, with 30-80% expression of DLK1.

In one embodiment, the present invention provides improved PE cell populations, with 20-80% expression of DLK1.

In one embodiment, the present invention relates to a synchronised cell population derived from human pluripotent stem cells presenting at least 70% of pancreatic endoderm cells expressing PDX1+/NKX6.1+ double positive.

In one embodiment, the present invention relates to a synchronised cell population derived from human pluripotent stem cells presenting at least 70% of pancreatic endoderm cells expressing PDX1+/NKX6.1+ double positive, wherein said cell population further expresses PTF1a.

In one embodiment, the present invention relates to a synchronised cell population derived from human pluripotent stem cells presenting at least 70% of pancreatic endoderm cells expressing PDX1+/NKX6.1+ double positive, wherein said cell population further expresses 5-30% DLK1.

In one embodiment, the present invention relates to a synchronised cell population derived from human pluripotent stem cells presenting at least 70% of pancreatic endoderm cells expressing PDX1+/NKX6.1+ double positive and expressing less than 1% NKX2.2.

In one embodiment, the present invention relates to a synchronised cell population derived from stem cells presenting less than 1% NKX2.2 positive.

In one embodiment the PE cells obtainable by the methods of the present invention are less than 1% positive for NKX2.2.

In one embodiment, the present invention relates to a method of differentiating DE into PE, wherein said PE cells are less than 1% NKX2.2 positive.

In one embodiment the present invention provides a more homogenous and synchronised pancreatic endoderm cell population, i.e., with lower induction of premature endocrine differentiation at the PE stage, marked by a reduced expression of NGN3 and NeuroD.

In one embodiment, the present invention relates to pancreatic endoderm cells population obtainable by the methods of the present invention, with reduced expression of NGN3 and NeuroD.

In one embodiment, the present invention relates to pancreatic endoderm cells population obtainable by the methods of the present invention, with at least 2 fold reduced expression of NGN3 and NeuroD.

In one embodiment, the present invention relates to pancreatic endoderm cells population obtainable by the methods of the present invention, wherein said PE population differentiate further into beta cells with at least 40% C-PEP+/ NKX6.1+ double positive.

Endocrine Progenitor Cells (EP Cells)

Endocrine progenitor cells are characterised by expression of markers NGN3, NeuroD and NKX2.2, hallmarks for EP cells committed to an endocrine cell fate.

As used herein, an "EP cell population" is a population of pancreatic beta-cell precursors in which at least 5% of the cell population are NKX6.1/NKX2.2 double positive.

"NGN3" as used herein, is a member of the neurogenin family of basic loop-helix-loop transcription factors.

"NKX2.2" and "NKX6.1" as used herein are members of the NKX transcription factor family.

"NeuroD" as used herein is a member of the NeuroD family of basic helix-loop-helix (bHLH) transcription factors.

Beta Cells

As used herein the term "beta-cells" refers to cells that reside within small cell clusters called islets of Langerhans in the pancreas. Beta cells are characterized by the co-expression of INS/NKX6.1 and C-PEP/NKX6.1.

Beta-cells respond to high blood glucose levels by secreting the peptide hormone insulin (INS), which acts on other tissues to promote glucose uptake from the blood, for example in the liver where it promotes energy storage by glycogen synthesis.

In one embodiment, the EP cells obtainable by further induction of the PE cells obtained by the method according to the invention are further differentiated into insulin producing cells, optionally together with cells differentiated towards glucagon, somatostatin, pancreatic polypeptide, and/or ghrelin producing cells.

As used herein, "insulin producing cells" refers to cells that produce and store or secrete detectable amounts of insulin. "Insulin producing cells" can be individual cells or collections of cells.

In one embodiment, the present invention provides an improved PE cell population that result in induction of a Beta like cell population with increased expression of C-PEP+/NKX6.1+.

Retinoic Acid Receptor (RAR) Antagonist

Retinoic acid receptor antagonists selectively counteract effects of retinoids on one or more of the retinoic acid receptor subtypes, RARα, RARβ and RARγ.

AGN 193109 is an orally active retinoic acid receptor (RAR) antagonist that targets all three RAR subtypes with higher affinity (RARα/β/γ Kd=2 nM) than all-trans retinoic acid/ATRA (RARα/β/γ Kd=9/12/19 nM). AGN 193109 potently antagonizes against ATRA-induced transcription in RARα, RARβ, and RARγ transfected CV-1 cells (by 85%, 62%, and 100%, respectively, by equal molar AGN 193109 against ATRA). AGN 193109 is also widely employed to block RAR-mediated physiological and pathological processes in mice and rats in vivo via oral (1-10 mg/kg) or topical (0.3-36 μmol/kg) administration.

Non-limiting examples of RAR antagonists include AGN193109, AGN 194431, AGN 194301, SR 11335, BMS 453, BMS 195614, LE 135, LG 100815, MM11253, CD 2665, ER 50891.

In one embodiment, the RAR antagonist is selected from the group selected from, but not limited to AGN193109, AGN 194431, AGN 194301, SR 11335, BMS 453, BMS 195614, LE 135, LG 100815, MM11253, CD 2665 and ER 50891.

In one embodiment the RAR antagonist is AGN193109.

In one embodiment, the present invention relates to a method of differentiating definitive endoderm cells derived from human pluripotent stem cells into pancreatic endoderm precursor cells comprising the step of culturing definitive endoderm in a culture medium comprising a retinoic acid receptor (RAR) antagonist.

In one embodiment, the present invention relates to a method of differentiating definitive endoderm cells derived from human pluripotent stem cells into pancreatic endoderm precursor cells comprising the step of culturing definitive endoderm in a culture medium comprising AGN 193109.

In one embodiment, the present invention relates to a method of differentiating DE into PE, comprising the first step of culturing DE in a culture medium comprising a RAR antagonist to obtain pancreatic endoderm precursors followed by a second step of culturing the pancreatic endoderm precursors in a cell culture medium comprising a RAR agonist.

In one embodiment, the present invention relates to a method of differentiating DE into PE, comprising the first step of culturing DE in a culture medium comprising AGN 193109 to obtain pancreatic endoderm precursors followed by a second step of culturing the pancreatic endoderm precursors in a cell culture medium comprising AM580.

In one embodiment, the present invention relates to a method of differentiating DE into PE, comprising the first step of culturing DE in a culture medium comprising a RAR antagonist to obtain pancreatic endoderm precursors, followed by a second step of culturing the pancreatic endoderm precursors in a cell culture medium comprising a RAR agonist, fibroblast growth factor and a Rock inhibitor and optionally a BMP inhibitor.

In one embodiment, the present invention relates to a method of differentiating DE into PE, comprising a first step of culturing DE in a culture medium comprising a RAR antagonist to obtain pancreatic endoderm precursors, followed by a second step of culturing the pancreatic endoderm precursors in a cell culture medium comprising a RAR agonist, FGF2 and Tiger or Y27632 and optionally LDN193189.

In one embodiment the present invention relates to the use of a RAR antagonist to induce pancreatic endoderm precursor cells from definitive endoderm derived from human pluripotent stem cells.

In one embodiment the present invention relates to the use of a RAR antagonist to induce pancreatic endoderm precursor cells from definitive endoderm derived from human pluripotent stem cells, followed by treatment of the pancreatic endoderm precursor cells with a RAR agonist to induce pancreatic endoderm.

In one embodiment, the method of the present invention comprises a RAR antagonist in a concentration in the range of 0.5-100 μM, 1-50 μM, 1-300 μM, 1-250 μM, 1-20 μM, 3-17 μM, 5-15 μM or 7-12 μM.

In one embodiment, the method of the present invention comprises a RAR antagonist in a concentration in the range of 0.5-100 μM.

In one embodiment, the method of the present invention comprises a RAR antagonist in a concentration in the range of 0.5-50 μM.

In one embodiment, the method of the present invention comprises a RAR antagonist in a concentration in the range of 0.5-30 μM.

In one embodiment, the method of the present invention comprises a RAR antagonist in a concentration in the range of 0.5-25 μM.

In one embodiment, the method of the present invention comprises a RAR antagonist in a concentration in the range of 0.5-20 μM.

In one embodiment, the method of the present invention comprises a RAR antagonist in a concentration in the range of 1-20 μM.

In one embodiment, the method of the present invention comprises a RAR antagonist in a concentration in the range of 10-20 μM.

In one embodiment, the method of the present invention comprises a RAR antagonist in a concentration in the range of 7-12 μM.

In one embodiment, the method of the present invention comprises a RAR antagonist in a concentration of about 10 μM.

In one embodiment, the method of the present invention comprises a RAR antagonist in a concentration of about 15 μM.

In one embodiment, the method of the present invention comprises a RAR antagonist in a concentration of about 20 μM.

In one embodiment the present invention relates to the use of a RAR antagonist followed by use of a RAR agonist, to induce pancreatic endoderm cells from definitive endoderm cells derived from human pluripotent stem cells.

In one embodiment the present invention relates to the use of a RAR antagonist in a concentration in the range of 0.5-100 μM, followed by use of a RAR agonist, to induce pancreatic endoderm cells from definitive endoderm cells derived from human pluripotent stem cells.

In one embodiment the present invention relates to the use of a RAR antagonist in a concentration of 10 μM to induce pancreatic endoderm precursor cells from definitive endoderm cells derived from human pluripotent stem cells.

In one embodiment the present invention relates to the use of a RAR antagonist in a concentration of 10 μM, followed by use of a RAR agonist, to induce pancreatic endoderm cells from definitive endoderm cells derived from human pluripotent stem cells.

In one embodiment the present invention relates to the use of a RAR antagonist in a concentration of 20 μM to induce pancreatic endoderm precursor cells from definitive endoderm cells derived from human pluripotent stem cells.

In one embodiment the present invention relates to the use of a RAR antagonist in a concentration of 20 μM, followed by use of a RAR agonist, to induce pancreatic endoderm cells from definitive endoderm cells derived from human pluripotent stem cells.

In one embodiment the present invention relates to the use of a RAR antagonist in combination with LDN followed by AM580 to induce pancreatic endoderm cells from definitive endoderm cells derived from human pluripotent stem cells.

In one embodiment, the present invention relates to the use of a RAR antagonist to improve the synchronisation of the pancreatic endoderm precursor cells, before inducing the pancreatic endoderm cells by treating the pancreatic endoderm precursor cells with a RAR agonist.

In one embodiment, the present invention relates to a method of differentiating DE into PE, comprising the first step of culturing DE in a culture medium comprising a RAR antagonist to obtain pancreatic endoderm precursors followed by a second step of culturing the pancreatic endoderm precursors in a cell culture medium comprising a RAR agonist, wherein said first step has the duration of one hour to six days or 1 to 4 days.

In one embodiment, the present invention relates to a method of differentiating DE into PE, comprising the first step of culturing DE in a culture medium comprising a RAR antagonist to obtain pancreatic endoderm precursors followed by a second step of culturing the pancreatic endoderm precursors in a cell culture medium comprising an RAR agonist, wherein said first step has the duration of two days.

In one embodiment, the present invention relates to a method of differentiating DE into PE, comprising the first step of culturing DE in a culture medium comprising a RAR antagonist to obtain pancreatic endoderm precursors followed by a second step of culturing the pancreatic endoderm precursors in a cell culture medium comprising an RAR agonist, wherein said first step has the duration of less than two days.

Retinoic Acid Receptor (RAR) Agonist

Retinoic receptor agonists selectively bind to and activate one or more of the retinoic acid receptor subtypes, RARα, RARAβ and RARγ.

Non-limiting examples of RAR agonists include AM580, All-trans retinoic acid, 9-cis retinoic acid, AC 261066, AC 55649, Adapalene, AM 80, BMS 753, BMS 961, CD 1530, CD 2314, CD 437, Ch 55, Isotretinoin, Tazarotene, TTNTB and EC19.

In one embodiment the RAR agonist is AM580.

In one embodiment the present invention relates to the use of a RAR agonist in a concentration in the range of 00.5-10 μM, preceded by a RAR antagonist, to induce pancreatic endoderm cells from human pluripotent stem cells.

In one embodiment the present invention relates to the use of a RAR agonist in a concentration 1 μM, preceded by a RAR antagonist, to induce pancreatic endoderm cells from human pluripotent stem cells.

In one embodiment the present invention relates to the use of a RAR agonist in a concentration 10 μM, preceded by a RAR antagonist, to induce pancreatic endoderm cells from human pluripotent stem cells.

BMP Inhibitor

Bone morphogenetic proteins (BMPs) are signalling molecules that act locally on target cells to affect cell survival, proliferation, and differentiation. While first identified as bone-inducing agents, BMPs are now known to affect the formation and function of many organ systems. BMP receptor antagonists or BMP inhibitors specifically inhibit BMP signalling by inhibiting Smad1/5/8 phosphorylation by ALK1, ALK2, ALK3 and ALK6.

Non-limiting examples of BMP inhibitors include LDN 193189, dorsomorphine, noggin, chordin, LDN 212854, LDN 214117, ML 347, DMH1, DMH2 and K 02288.

In one embodiment the BMP inhibitor is LDN193189.

In one embodiment the present invention relates to the use of a RAR antagonist in combination with a BMP inhibitor LDN, wherein said BMP inhibitor is in the concentration range of 25-200 nM.

In one embodiment the present invention relates to the use of a RAR antagonist in combination with a BMP inhibitor LDN, wherein said BMP inhibitor is in the concentration of 50 nM.

In one embodiment the present invention relates to the use of a RAR antagonist in combination with a BMP inhibitor LDN, wherein said BMP inhibitor is in the concentration of about 50 nM.

ROCK Inhibitor

Rho-associated coiled-coil containing kinases (ROCK) is an effector of the RhoA small GTPase and belongs to the AGC family of serine/threonine kinases. ROCK kinases have many functions including cell contraction, migration, apoptosis, survival, and proliferation. IRho-associated, coiled-coil containing protein kinase ROCK inhibitors are a series of compounds that target and inhibit rho kinase.

In one embodiment the Rock inhibitor is Tiger or Y27632.

In one embodiment the present invention relates to the use of a RAR antagonist in combination with a Rock inhibitor, wherein said Rock inhibitor is in the concentration range of 1-20 μM.

In one embodiment the present invention relates to the use of a RAR antagonist in combination with a Rock inhibitor, wherein said Rock inhibitor is in the concentration of 5 μM.

bFGF

Basic Fibroblast Growth Factor (FGF), also known as FGF2, is a growth factor and signalling protein encoded by the FGF2 gene.

In one embodiment the growth factor is bFGF.

In one embodiment the present invention relates to the use of a RAR antagonist in combination with bFGF, wherein said bFGF is in the concentration range of 25-200 nM.

Bioreactor

15

Suspension culture bioreactors allow for large-scale expansion and differentiation of stem cells and/or their progeny in a controlled and reproducible culture system. These systems offer a homogeneous culture environment where conditions such as temperature, pH, and oxygen concentration can be monitored and controlled. Furthermore, these systems permit the production of large numbers of cells under consistent culture conditions, and with minimal culture variability.

Culture Medium/Composition

A solid, liquid or semi-solid designed to support the growth of microorganisms or cells.

Different types of commercial media are used for growing different types of cells.

In one embodiment the present invention relates to a culture medium comprising retinoic acid receptor (RAR) antagonist for generating pancreatic endoderm precursors from definitive endoderm derived from human pluripotent stem cells.

In one embodiment the present invention relates to a culture medium comprising AGN 193109 for generating pancreatic endoderm precursors from definitive endoderm derived from human pluripotent stem cells.

In one embodiment the present invention relates to a culture medium comprising retinoic acid receptor (RAR) antagonist, followed by RAR agonist for generating pancreatic endoderm/PDX1+/NKX6.1+ from definitive endoderm derived from human pluripotent stem cells.

In one embodiment the present invention relates to a culture medium comprising AGN 193109, followed by AM580 for generating pancreatic endoderm /PDX1+/ NKX6.1+ from definitive endoderm derived from human pluripotent stem cells.

In one embodiment the present invention relates to a culture medium comprising retinoic acid receptor (RAR) antagonist.

In one embodiment the present invention relates to a culture medium comprising retinoic acid receptor (RAR) antagonist, followed by addition of a retinoic acid receptor (RAR) agonist.

In another embodiment the present invention relates to a culture medium comprising retinoic acid receptor (RAR) antagonist and a BMP inhibitor, followed by addition of a retinoic acid receptor (RAR) agonist.

In another embodiment the present invention relates to a culture medium comprising retinoic acid receptor (RAR) antagonist, a BMP inhibitor and a Rock inhibitor, followed by addition of a retinoic acid receptor (RAR) agonist, and a Rock inhibitor.

In another embodiment the present invention relates to a culture medium comprising retinoic acid receptor (RAR) antagonist, a BMP inhibitor and a Rock inhibitor, followed by addition of a retinoic acid receptor (RAR) agonist, a Rock inhibitor and FGF2.

In one embodiment the present invention relates to a culture medium comprising retinoic acid receptor (RAR) antagonist, wherein said RAR antagonist is AGN 193109, followed by addition of a retinoic acid receptor (RAR) agonist, wherein said RAR agonist is AM580.

In one embodiment the present invention relates to a culture medium comprising retinoic acid receptor (RAR) antagonist, wherein said RAR antagonist is AGN 193109.

In one embodiment the present invention relates to a culture medium further comprising the BMP inhibitor LDN193189.

In one embodiment the present invention relates to a culture medium further comprising FGF2.

In one embodiment the present invention relates to a culture medium further comprising the Rock Inhibitor Tiger or Y27632.

In one embodiment the present invention relates to a composition comprising:

a) a culture medium comprising retinoic acid receptor (RAR) antagonist such as AGN 193109 b) definitive endoderm cells and/or pancreatic endoderm cells derived from human pluripotent stem cells.

Protocols

As used herein, the term "LDN stage" means 4 days from PE0-3 where LDN is added for first two days i.e. at PE0-PE1 and LDN and RAR antagonist are added at last 2 days i.e. PE2-PE3.

Cells differentiated to the DE stage in suspension culture in shaker flasks or bioreactors are continued in PE differentiation (WO2012/175633 which incorporated herein by reference in its entirety). AGN193109 is added to the culture medium during the LDN stage for two days. PE induction in the second stage of the PE differentiation protocol is performed with no changes to the standard protocol (WO2014/033322 which incorporated herein by reference in its entirety).

A protocol for obtaining pancreatic cells from stem cells is exemplified by, but not limited to, the protocols described in D'Amour, K. A. et al. (2006); Jiang, J. et al. (2007); Kroon, E. et al. (2008).

A protocol for obtaining pancreatic cells from somatic cells or somatic cells induced to de-differentiate into pluripotent cells such as ES like-cells is exemplified by, but not limited to, the protocols described in Aoi, T. et al. (2008); D'Amour, K. A. et al. (2006); Jiang, J. et al. (2007); Kroon, E. et al. (2008); Takahashi, K. et al. (2007); Takahashi, K., and Yamanaka, S. (2006) and Wernig, M. et al. (2007).

Unless otherwise indicated in the specification, terms presented in singular form also include the plural situation.

The invention is further described by the following non-limiting embodiments:

1. A method of differentiating definitive endoderm cells derived from human pluripotent stem cells into pancreatic endoderm precursor comprising a step of culturing definitive endoderm (DE) in a culture medium comprising a retinoic acid receptor (RAR) antagonist.

2. The method according to embodiment 1, wherein said method further comprises a step of culturing the pancreatic endoderm precursors in a cell culture medium comprising a RAR agonist, thereby inducing pancreatic endoderm (PE), wherein said cells are NKX6.1+/ PDX1+ double positive.

3. The method according to embodiment 2, wherein said culture medium optionally further comprises a BMP inhibitor, growth factor and/or a Rock inhibitor.

4. The method according to any one of the preceding embodiments, wherein said retinoic acid receptor (RAR) antagonist is AGN 193109.

5. The method according to any one of the preceding embodiments, wherein said RAR agonist is AM580.

6. The method according to embodiments 3-5, wherein said optional BMP inhibitor is LDN193189.

7. The method according to embodiments 3-5, wherein said optional growth factor is bFGF2.

8. The method according to embodiments 3-5, wherein said optional Rock inhibitor is Tiger or Y27632.

9. The method according to any one of the preceding embodiments, wherein said human pluripotent stem cells are embryonic stem cells or induced pluripotent stem cells.

10. The method according to any one of the preceding embodiments, wherein the concentration of said retinoic acid receptor (RAR) antagonist is 0.5-100 µM, 1-50 µM, 1-300 µM, 1-250 µM, 1-20 µM, 3-17 µM, 5-15 µM or 7-12 µM.

11. The method according to any one of the preceding embodiments, wherein the concentration of said retinoic acid receptor (RAR) antagonist is 0.5-100 µM.

12. The method according to any one of the preceding embodiments, wherein the concentration of said retinoic acid receptor (RAR) antagonist is 0.5-50 µM.

13. The method according to any one of the preceding embodiments, wherein the concentration of said retinoic acid receptor (RAR) antagonist is 0.5-30 µM. 14. The method according to any one of the preceding embodiments, wherein the concentration of said retinoic acid receptor (RAR) antagonist is 0.5-25 µM.

15. The method according to any one of the preceding embodiments, wherein the concentration of said retinoic acid receptor (RAR) antagonist is 0.5-20 µM.

16. The method according to any one of the preceding embodiments, wherein the concentration of said retinoic acid receptor (RAR) antagonist is 1-20 µM.

17. The method according to any one of the preceding embodiments, wherein the concentration of said retinoic acid receptor (RAR) antagonist is 10-20 µM.

18. The method according to any one of the preceding embodiments, wherein the concentration of said retinoic acid receptor (RAR) antagonist is 7-12 µM.

19. The method according to any one of the preceding embodiments, wherein the concentration of said retinoic acid receptor (RAR) antagonist is of 10 µM.

20. The method according to any one of the preceding embodiments, wherein the concentration of said retinoic acid receptor (RAR) antagonist is of 15 µM.

21. The method according to any one of the preceding embodiments, wherein the concentration of said retinoic acid receptor (RAR) antagonist is of 20 µM.

22. The method according to any one of the preceding embodiments, wherein said step of embodiment 1 has the duration of one hour to six days or 1 to 4 days.

23. The method according to any one of the preceding embodiments, wherein said step of embodiment 1 has the duration of two days.

24. The method according to any one of the preceding embodiments, wherein said step of embodiment 1 has the duration of less than two days.

25. The method according to any one of the preceding embodiments, wherein at least 5% of the said pancreatic endoderm cells co-express PDX1 and NKX6.1.

26. The method according to any one of the preceding embodiments, wherein said pancreatic endoderm cells are at least 5%, at least 10%, 10-30%, 10-40%, 5-70%, 10-80% or 5-100% PDX1+/NKX6.1+ double positive.

27. The method according to any one of the preceding embodiments, wherein said pancreatic endoderm cells are at least 70% PDX1+/NKX6.1+ double positive.

28. The method according to any one of the preceding embodiments, wherein said pancreatic endoderm cells are at least 80% PDX1+/NKX6.1+ double positive.

29. The method according to any one of the preceding embodiments, wherein said pancreatic endoderm cells are at least 90% PDX1+/NKX6.1+ double positive.

30. The method according to any one of the preceding embodiments, wherein said pancreatic endoderm cells are at least 95% PDX1+/NKX6.1+ double positive.

31. The method according to any one of the preceding embodiments, wherein said pancreatic endoderm cells are at least 98% PDX1+/NKX6.1+ double positive.

32. The method according to any one of the preceding embodiments, wherein said definitive endoderm cells are SOX17+/FOXA2+/CXCR4+ triple positive.

33. The method according to any one of the preceding embodiments, wherein said pancreatic endoderm cells are less than 1% NKX2.2 positive.

34. The method according to any one of the preceding embodiments, wherein said method is able to rescue suboptimal PE differentiation.

35. The method according to any one of the preceding embodiments, wherein said method comprises a LDN stage.

36. The method according to any one of the preceding embodiments, wherein said method is shorter than the standard method, wherein the LDN stage is two days.

37. The method according to any one of the preceding embodiments, comprising incubating the DE cells in vitro.

38. The method according to any one of the preceding embodiments 1-35, comprising incubating the DE cells in vivo.

39. The method according to any one of the preceding embodiments 1-35, further comprising isolating the differentiated cell.

40. The method according to any one of the preceding embodiments 1-35, further comprising storing the differentiated cell.

41. A pancreatic endoderm cell wherein said pancreatic endoderm cell is a product of the method according to any one of the preceding embodiments.

42. A pancreatic endoderm cell culture or pancreatic endoderm cell population comprising a plurality of cells according to embodiment 41.

43. A pancreatic endoderm cell obtainable by the method of embodiments 1-40.

44. The pancreatic endoderm cell of embodiment 43, with increased expression of Nkx6.1+/Pdx1+ double positive.

45. The pancreatic endoderm cell of embodiment 43, wherein said pancreatic endoderm cells are at least 70% PDX1+/NKX6.1+ double positive.

46. The pancreatic endoderm cell of embodiment 43, wherein said pancreatic endoderm cells are at least 80% PDX1+/NKX6.1+ double positive.

47. The pancreatic endoderm cell of embodiment 43, wherein said pancreatic endoderm cells are at least 90% PDX1+/NKX6.1+ double positive.

48. The pancreatic endoderm cell of embodiment 43, wherein said pancreatic endoderm cells are at least 95% PDX1+/NKX6.1+ double positive.

49. The pancreatic endoderm cell of embodiment 43, wherein said pancreatic endoderm cells are at least 98% PDX1+/NKX6.1+ double positive.

50. The pancreatic endoderm cell of embodiment 43, wherein said pancreatic endoderm cells are 80-100% PDX1+/NKX6.1+ double positive.

51. The pancreatic endoderm cell of embodiment 43, wherein said pancreatic endoderm cells are 90-100% PDX1+/NKX6.1+ double positive.

52. The pancreatic endoderm cell of embodiment 43, wherein said pancreatic endoderm cells are less than 1% NKX2.2 positive.

53. The pancreatic endoderm cell of embodiment 43, with reduced expression of NGN3 and NeuroD.

54. The pancreatic endoderm cell of embodiment 43, with 2 fold reduced expression of NGN3 and NeuroD.

55. The pancreatic endoderm cell of embodiment 43, wherein said PE differentiate further into beta cells with at least 40% C-PEP+/NKX6.1+.

56. The pancreatic endoderm cell of embodiment 43, wherein said PE is induced more selectively, more homogeneously and more efficiently into an EP cell and further into a Beta cell.

57. The pancreatic endoderm cell of embodiments 43-56, wherein said PE cell is induced in vitro or in vivo.

58. The pancreatic endoderm cell of embodiment 57, wherein said PE cell is induced in vitro.

59. The pancreatic endoderm cell of embodiment 57, wherein said PE cell is induced in vivo.

60. The pancreatic endoderm cell according to any one of embodiments 43-59, for further differentiation into beta cells, for use as a medicament.

61. The pancreatic endoderm cell according to any one of embodiments 43-59, for further differentiation into a beta cell, for use a medicament in the treatment of diabetes by administering stem cells or tissue or organ derived from stem cells to a subject or by grafting stem cells or tissue or organ derived from stem cells into a subject or by transplanting stem cells or tissue or organ derived from stem cells into a subject.

62. A culture medium comprising retinoic acid receptor (RAR) antagonist for generating pancreatic endoderm precursors from definitive endoderm cells derived from human pluripotent stem cells.

63. The culture medium of embodiment 62, further comprising a retinoic acid receptor (RAR) agonist for generating pancreatic endoderm, wherein said pancreatic endoderm cells are at least 70% PDX1+/NKX6.1+ double positive.

64. The culture medium of embodiment 62, further comprising a BMP inhibitor.

65. The culture medium of embodiment 62, further comprising a Rock inhibitor.

66. The culture medium of embodiment 63, further comprising a FGF2.

67. The culture medium of embodiment 62, wherein said retinoic acid receptor (RAR) antagonist is AGN 193109.

68. The culture medium of embodiment 63, wherein said retinoic acid receptor (RAR) agonist is AM580.

69. The culture medium of embodiment 62, wherein said further BMP inhibitor is LDN193189.

70. The culture medium of embodiment 62, wherein the Rock inhibitor is Tiger or Y27632.

71. Use of a retinoic acid receptor (RAR) antagonist in a concentration in the range of 0.5-100 μM to induce pancreatic endoderm cells from definitive endoderm cells derived from human pluripotent stem cells.

72. The use of embodiment 71, wherein said retinoic acid receptor (RAR) antagonist is in a concentration in the range of 0.5-50 μM to induce pancreatic endoderm cells from definitive endoderm cells derived from human pluripotent stem cells.

73. The use of embodiment 71, wherein said retinoic acid receptor (RAR) antagonist is in a concentration in the range of 0.5-30 μM to induce pancreatic endoderm cells from definitive endoderm cells derived from human pluripotent stem cells.

74. The use of embodiment 71, wherein said retinoic acid receptor (RAR) antagonist is in a concentration in the range of 0.5-20 μM to induce pancreatic endoderm cells from definitive endoderm cells derived from human pluripotent stem cells.

75. The use of embodiment 71, wherein the retinoic acid receptor (RAR) antagonist concentration is in the range of 10-20 μM.

76. The use of embodiment 71, wherein the retinoic acid receptor (RAR) antagonist concentration is about 10 μM.

77. The use of embodiment 71, wherein the retinoic acid receptor (RAR) antagonist concentration is about 20 μM.

78. Use of the retinoic acid receptor (RAR) antagonist AGN193109 in a concentration in the range of 0.5-100 μM to induce pancreatic endoderm precursor cells from definitive endoderm cells derived from human pluripotent stem cells.

79. The use of embodiment 78, wherein the retinoic acid receptor (RAR) antagonist AGN193109 is in a concentration of 0.5-50 μM.

80. The use of embodiment 78, wherein the retinoic acid receptor (RAR) antagonist AGN193109 is in a concentration of 0.5-30 μM.

81. The use of embodiment 78, wherein the retinoic acid receptor (RAR) antagonist AGN193109 is in a concentration of 0.5-20 μM.

82. The use of embodiment 78, wherein the retinoic acid receptor (RAR) antagonist AGN193109 is in a concentration of about 10 μM.

83. The use of embodiment 78, wherein the retinoic acid receptor (RAR) antagonist AGN193109 is in a concentration of about 20 μM.

84. Use of the retinoic acid receptor (RAR) antagonist AGN193109 in combination with a BMP inhibitor, followed by AM580 in combination with a FGF2 and/or a Rock inhibitor, to induce pancreatic endoderm cells from human pluripotent stem cells.

85. The use of embodiment 84, said BMP inhibitor is LDN193189.

86. The use of embodiment 84, said Rock inhibitor is Tiger or Y27632.

87. A synchronised pancreatic endoderm cell population derived from human pluripotent stem cells presenting at least 70% of pancreatic endoderm cells expressing PDX1+/NKX6.1+ double positive.

88. The synchronised pancreatic endoderm cell population of embodiment 87, wherein said cell population further expresses PTFa.

89. The synchronised pancreatic endoderm cell population of embodiment 87, wherein said cell population further expresses at least 30% DLK1.

90. The synchronised pancreatic endoderm cell population of embodiment 87, wherein said cell population further expresses 20-80% DLK1.

91. The synchronised pancreatic endoderm cell population of embodiment 87, wherein said cell population further expresses at least 30-80% DLK1.

92. The synchronised pancreatic endoderm cell population of embodiment 87, wherein said cell population expresses less than 1% NKX2.2.

93. The synchronised pancreatic endoderm cell population of embodiment 87, with reduced expression of NGN3 and NeuroD.

94. The synchronised pancreatic endoderm cell population of embodiment 87, with 2 fold reduced expression of NGN3 and NeuroD.

95. The synchronised pancreatic endoderm cell population of embodiment 87, wherein said PE differentiate further into beta cells with at least 40% C-PEP+/ NKX6.1+.

96. The synchronised pancreatic endoderm cell population of embodiments 87-95, wherein said PE is induced more selectively, more homogeneously and more efficiently into an EP cell and further into a Beta cell.

97. The synchronised pancreatic endoderm cell population of embodiments 87-95, wherein said PE cell is induced in vitro or in vivo.

98. The synchronised pancreatic endoderm cell population of embodiment 97, wherein said PE cell is induced in vitro.

99. The synchronised pancreatic endoderm cell population of embodiment 97, wherein said PE cell is induced in vivo.

100. The synchronised pancreatic endoderm cell population of embodiments 87-99, for further differentiation into beta cells, for use as a medicament.

101. The synchronised pancreatic endoderm cell population of embodiments 87-100, for further differentiation into a beta cell, for use a medicament in the treatment of diabetes by administering stem cells or tissue or organ derived from stem cells to a subject or by grafting stem cells or tissue or organ derived from stem cells into a subject or by transplanting stem cells or tissue or organ derived from stem cells into a subject.

102. Use of a pancreatic endoderm cell of embodiments 41-61 or synchronised cell population of embodiments 87-101, in the preparation of a medicament for stimulating or enhancing tissue or organ formation and/or regeneration and/or repair in a subject.

103. A composition comprising:
a. a culture medium comprising retinoic acid receptor (RAR) antagonist (AGN 193109)
b. definitive endoderm cells and/or pancreatic endoderm cells derived from human pluripotent stem cells.

104. A pharmaceutical composition comprising a pancreatic endoderm cell, for further differentiation of PE cell into a beta cell, or cell population thereof, according to any one of embodiments 41-61 or 87-101 and a pharmaceutically acceptable carrier.

105. A composition comprising a pancreatic endoderm cell, for further differentiation of PE cell into a beta cell, or cell population thereof, according to any one of embodiments 41-61 or 87-101 and a biocompatible scaffold or matrix.

106. A bioreactor comprising a pancreatic endoderm cell obtained by the methods of embodiments 1-40.

107. A method of treating a patient with type 1 diabetes comprising the step of administering cells according to embodiments 41-61 or 87-101, cells obtained according to the method of embodiments 1-40 or cells of embodiments 1-40 for further differentiation into beta cells.

108. The method of treating a patient with type 1 diabetes comprising the step of administering cells according to embodiments 41-61 or 87-101, which are for further differentiation into beta cells.

109. A method of prophylaxis or treatment of diabetes, said method comprising administering, transplanting or grafting to said subject an effective amount of the a pancreatic endoderm cell or pancreatic endoderm cell population according to any one of embodiments 41-61 or 87-101, which has been further differentiated to beta cells, thereby preventing or treating diabetes in the subject.

110. A kit for regenerating and/or repairing and/or building a tissue or an organ, wherein said kit comprises:
(i) a pancreatic endoderm cell or pancreatic endoderm cell population according to any one of embodiments 41-61 or 87-101, for further differentiation into beta cells,
(ii) a biocompatible scaffold or matrix;
(iii) optionally, at least one growth factor or functional fragment thereof;
(iv) optionally, an agent selected from the group consisting of a BMP inhibitor, growth factor and/or a Rock inhibitor and combinations thereof; and
(iv) optionally, directions for preparing, maintaining and/or using the cells including any cell culture or tissue or organ derived therefrom.

Materials and Methods

List of Abbreviations

+ve: positive
BC: Beta Cell (e.g. BC7: Day 7 of beta cell differentiation)
bFGF: basic Fibroblast Growth Factor (FGF) (also known as FGF2)
Cyc: Cyclopamine
db: double positive
DE: Definitive Endoderm
EP: Endocrine Progenitor
hBS: human Blastocyst derived Stem
hBSC; human Blastocyst-derived Stem Cells
hES: human Embryonic Stem
hESC: human Embryonic Stem Cells
hiPSC: human induced Pluripotent Stem Cells
hPSC: human Pluripotent Stem Cells
KOSR: Knock-out Serum Replacement
NKX6.1: NK6 homeobox 1
PDX1: Pancreatic and duodenal homeobox 1
PE: Pancreatic Endoderm (e.g. PE10: Day 10 of pancreatic endoderm differentiation)
PEST: Penicillin Streptomycin
PS: Pluripotent Stem
Rocki: Rho Kinase Inhibitor III
RT: Room Temperature
General Methods of Preparation
Culture of Pluripotent Stem Cells Human embryonic stem (hES) cells line SA121 (Cellectis) are expanded in DEF-CS culture medium (Takara BIO Europe) in fibronectin (Sigma) coated culture flasks (Corning) with 30 ng/ml bFGF (Peprotech) and 10 ng/ml noggin (Peprotech). Cells are single cell passaged with 10 μM Rock inhibitor Y-27632 (Sigma #Y0503) and seeded in shaker flasks or bioreactors (DASBOX, DASGIP, Eppendorf) at a density of 0.5-1 mio/ml and allowed to form clusters under constant stirring conditions.
Differentiation of Pluripotent Stem Cells into Definitive Endoderm (DE)

After 1-3 days in DEF-CS medium with daily medium change, the clusters are differentiated to DE as described in WO2012/175633 (which is incorporated herein by reference in its entirety). The cell clusters are washed once in RPM11640 (Gibco #61870) and treated with 2-7 μM CHIR99021 (Axon #1386) in RPM11640. After 24 hours the cells were washed with RPM11640 and treated with 25-100 ng/ml Activin A (Peprotech #120-14E) and 2% B27 (Invitrogen #17504-044) in RPM11640 for 3 days with medium change every 24 or 48 hours. Cells are maintained at 37° C. and 5% $CO_2$ in a humidified shaker incubator (Infors) during the differentiation to DE, or in a bioreactor system (DAS-BOX, DASGIP, Eppendorf). At the end of differentiation to DE, 95% of the population express SOX17 and less than 1% express the pluripotency marker OCT4.

Example 1

Differentiation of Definitive Endoderm to Pancreatic Endoderm is Improved with AGN193109 Added to the LDN Stage In the standard protocol for differentiation to pancreatic endoderm, clusters differentiated to DE are washed once in RPM11640 (Gibco #61870) and differentiated in the presence of LDN193189 (Stemgent 04-0074) and Rock-I (Sigma Y27632-Y0503) in RPM11640 with 12% KOSR (Gibco 10828-028) for 4 days, and then subjected to medium containing AM580 (ENZO/Biomol GR104-0025), bFGF (#100-18B, Peprotech) Jnkill (Calbiochem 420119) and Rock-I for 6-9 days as described in WO2014/033322 (which is incorporated herein by reference in its entirety). Medium was changed daily or every other day. At the end of PE differentiation clusters were analysed by flow cytometry or gene expression analysis (Nanostring). 10 µM AGN193109 (Tocris 5758) was added to the LDN stage of PE differentiation, whereas the remaining part of the protocol was unchanged.

The addition of 10 µM AGN 193109 for the last 2 days during the LDN stage (PE2-3) lead to a marked increase in the proportion of Pdx1/Nkx6.1 double positive pancreatic endoderm on day 10 of PE differentiation (PE10) (FIGS. 1A,B). With AGN193109 we observed at least 70% Pdx1/Nkx6.1 double positive, whereas this was around 40% in the standard condition, and less than 10% Pdx1/Nkx6.1 double negative cells.

Furthermore, it appears that AGN193109 addition as described is able to rescue an otherwise suboptimal PE differentiation, as we observe an increase from 20% to 75% Pdx1/Nkx6.1 double positive cells with AGN193109 treatment (FIG. 10).

Figure 2A:
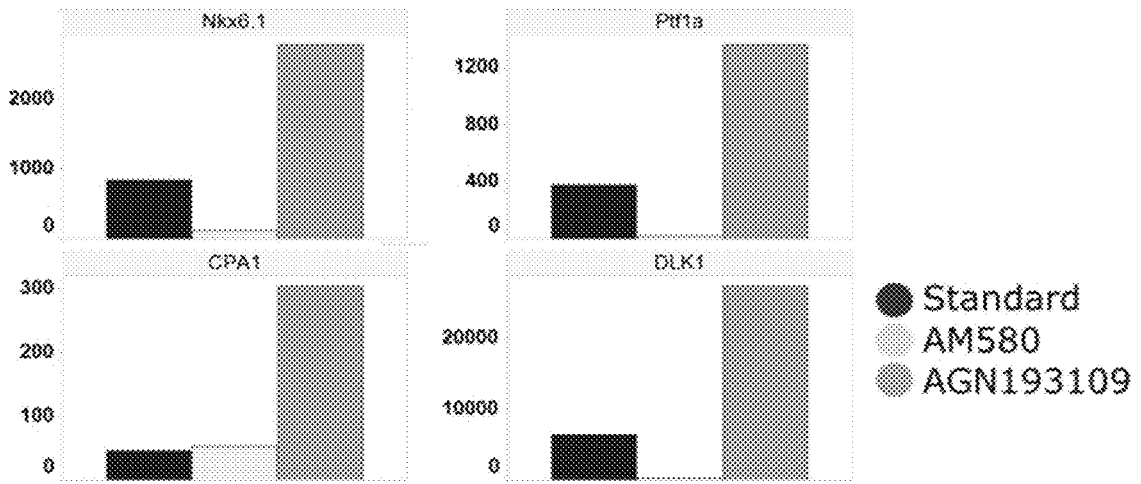
FIGS. 2A-B show the effect of AGN 193109 on the expression of markers of pancreatic endoderm.

We also observe an increase in other markers of pancreatic endoderm such as PTF1A, CPA1 and DLK1 with the addition of AGN 193109 (FIG. 2A). When instead activating RAR signalling with AM580 on PE2-3, we observe a marked down regulation of Nkx6.1, PTF1A and DLK1, pointing to the effect of AGN193109 being mediated specifically by inhibition of RAR signalling (FIG. 2A).

Figure 2B:
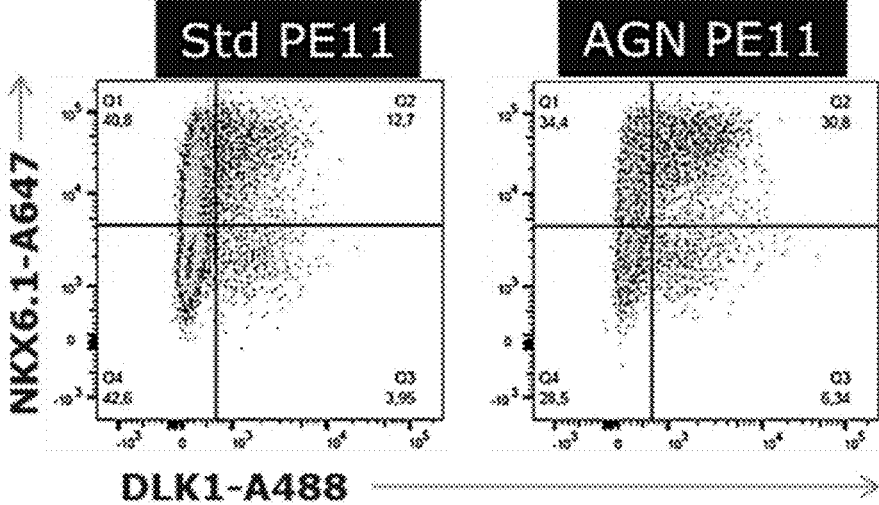

DLK1 is also confirmed by flow cytometry to be expressed in a higher percentage of pancreatic endoderm, when adding AGN 193103 on PE2-3 (31% vs 13%). We identify DLK1 as a marker of pancreatic endoderm primarily in cells expressing high levels of Nkx6.1 (FIG. 2B)

Figure 3A:
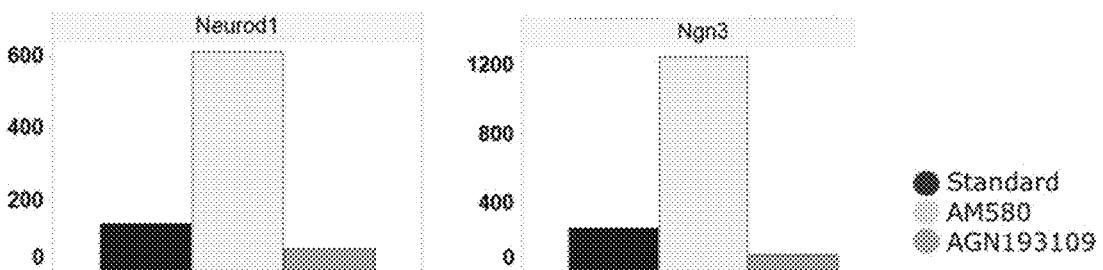
FIGS. 3A-B show the effect of AGN1931091 on premature endocrine differentiation on PE10.

In addition, the differentiation is more synchronized with a lower degree of premature endocrine differentiation at the PE stage, characterized by a lower expression of Ngn3 and NeuroD compared to the condition without AGN193109 addition (FIG. 3A). Again, it appears that the activation of RAR signalling by AM580 has the opposite effect, leading to a marked increase of Ngn3 and NeuroD1 already on PE10 (FIG. 3A).

Figure 3B:
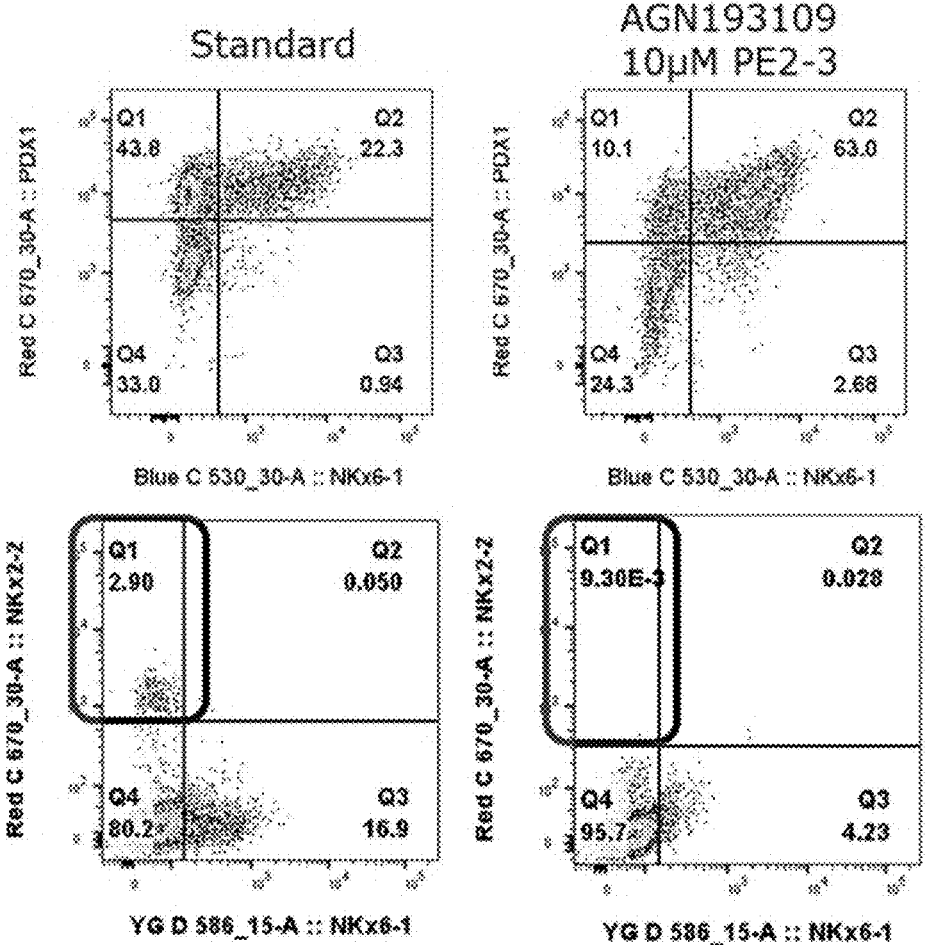

The percentage of Nkx2.2 positive cells, which marks cells specified to an endocrine fate, at the PE stage was reduced to less than 1% with AGN193109 treatment, compared with 2.9% in the control (FIG. 3B).

Figure 4:
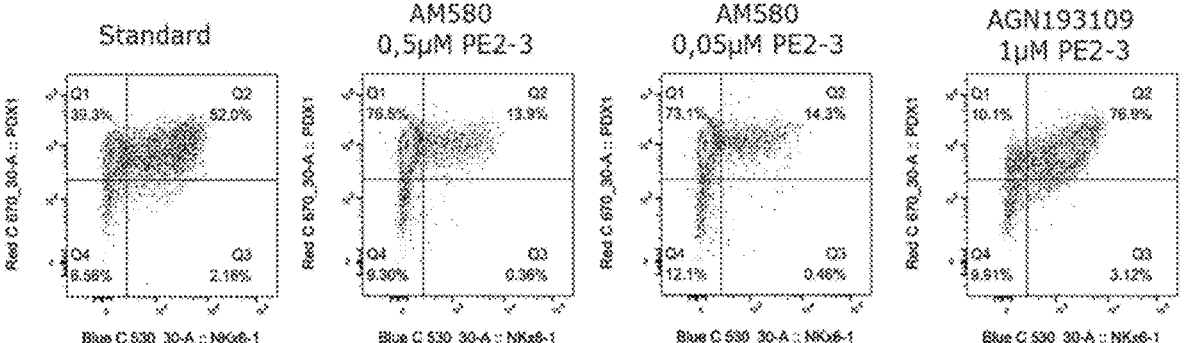
FIG. 4 shows the effect of RAR activation by AM580 and RAR inhibition by AGN 193109 on PE2-3 on pancreatic endoderm induction compared to the standard protocol, evaluated by a FACS analysis on Pdx1/Nkx6.1 on PE10.

As demonstrated on gene expression, we also demonstrate by flow cytometry that the effect of AGN193109 is likely a specific effect of retinoic acid receptor (RAR) inhibition. We observe an opposite phenotype by adding AM580, a RAR agonist, instead, namely a marked reduction in the proportion of PDX1/NKX6.1 double+ pancreatic endoderm on PE10 (FIG. 4A). With AGN193109 treatment the number of Pdx1/Nkx6.1 double positive increase from 52% to 76.9%, whereas it decreases to ~14% with AM580 treatment.

Figure 8:
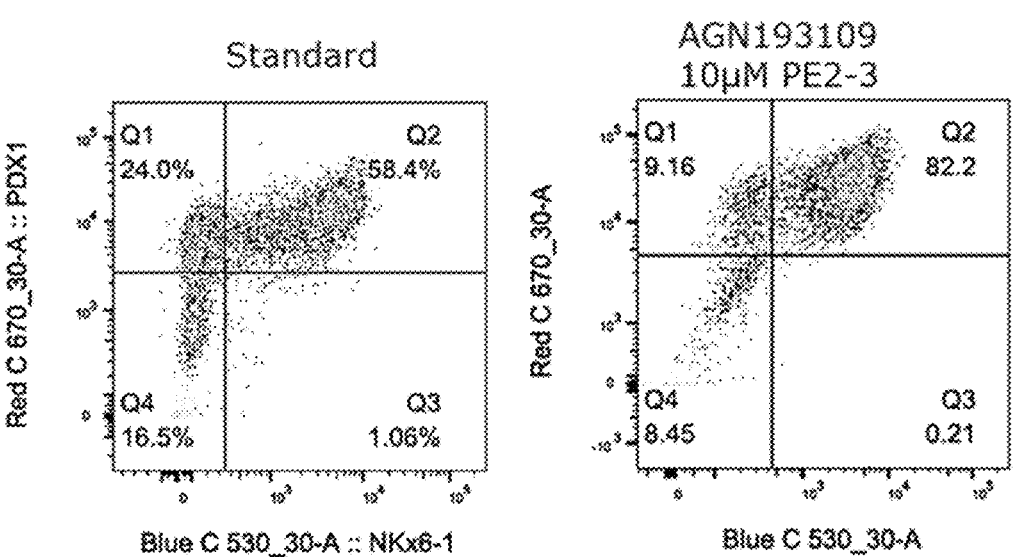
FIG. 8 shows the function of the protocol with AGN 193109 in bioreactors, evaluated by FACS analysis on Pdx1/Nkx6.1 on PE10. The figure show examples of 2 representative experiments run in 1 L tanks in bioreactors (DASgip, Eppendorf) with and without 10 μM AGN193109 addition on PE2-3.

The positive effect of AGN193109 can be reproduced in 1 L bioreactors (DASgip, Eppendorf). The data demonstrates that the AGN0193109 protocol modification is compatible with the bioractor format, and although the experiments were not run in parallel, the results suggest that AGN 193109 in the bioreactor format may offer an advantage on PE induction compared to the standard protocol (FIG. 8A). Using the standard protocol we obtained 58.4% Pdx1/Nkx6.1 double positive, whereas the number was 82.2 with AGN193109 treatment.

Figure 6A:
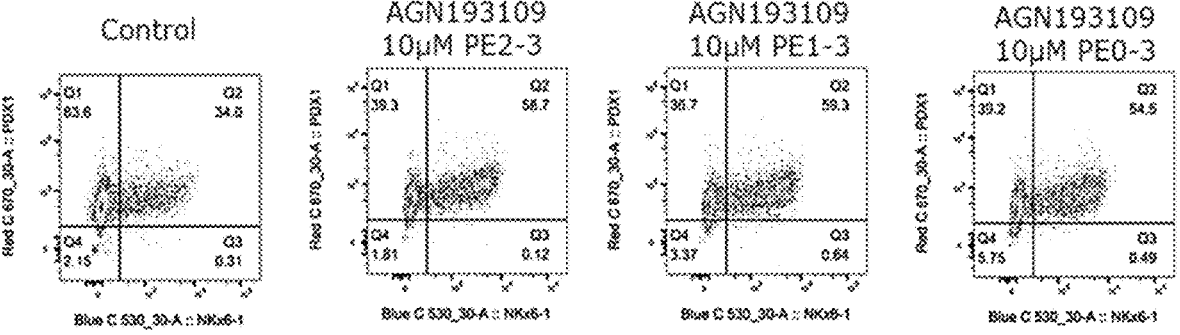
FIGS. 6A-B show the effect of the timing of AGN 193109, evaluated by a FACS analysis on Pdx1/Nkx6.1 on PE10. In one experiment we increase the exposure time of 10 μM AGN 193109 from 2 days (PE2-3) to 3 (PE1-3) or 4 days (PE0-3) during the 4 day LDN stage from PE0-3 (FIG. 6A). In another experiment we maintain a 2 day treatment with 10 μM AGN 193109 and shorten the LDN193109 (LDN) stage from 4 days to 3 days or 2 days (FIG. 6B).

The addition of AGN193109 can be extended from 2 to 4 days in the LDN stage without any negative effect on PE induction, as measured by Pdx1/Nkx6.1 double positive (FIG. 6A).

Figure 5A:
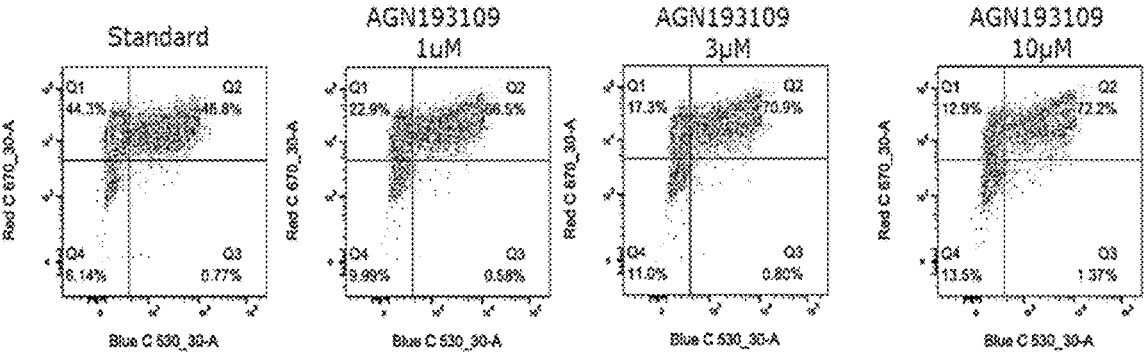
FIGS. 5A-B show the dose response effect of AGN 193109 on PE induction in 2 examples, evaluated by a FACS analysis on Pdx1/Nkx6.1 on PE10. In one experiment we tested the concentrations 1, 3 and 10 μM AGN 193109 on PE2-3 (FIG. 5A). In another experiment we tested the concentrations 0.5, 1, 10 and 20 μM AGN193109 on PE2-3 (FIG. 5B).
Figure 5B:
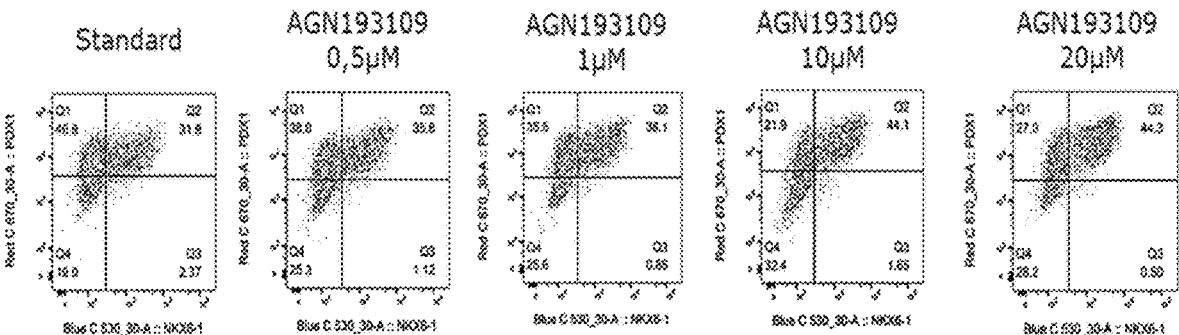
Figure 6B:
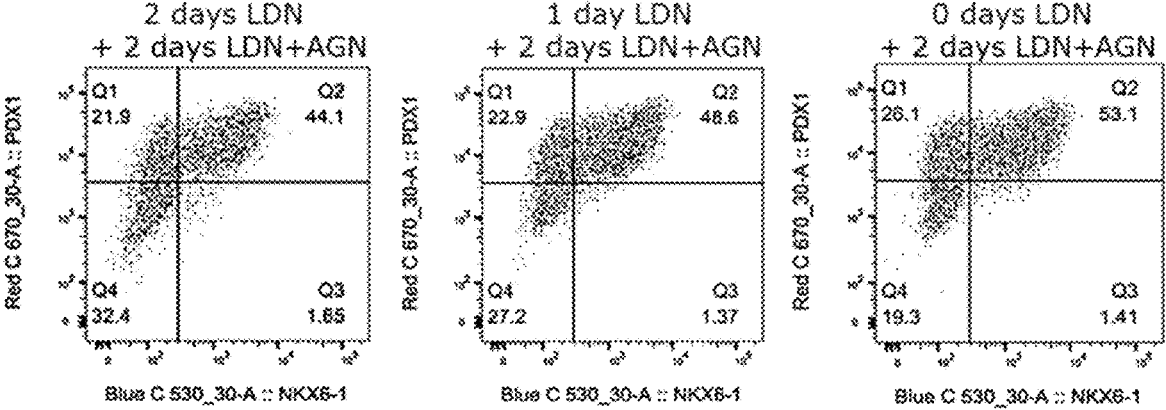

Very surprisingly, the length of the LDN stage can be reduced to only 2 days in the presence of AGN 193109, thus shortening the length of the protocol for induction of PE by 2 days (FIG. 6B). The effect of AGN193109 is dose-responsive and is documented in a range from 0.5 µM to 20 µM. We observe an increase in the number of Pdx1/Nkx6.1 double positive cells with increasing concentrations, and a decrease in Pdx1-only positive cells (FIG. 5A). We observe no additional effect of increasing the concentration from 10 µM to 20 µM (FIG. 5B).

Example 2

Improved Differentiation to Cpep/Nkx6.1 Double Positive Beta Like Cells following AGN193109 Addition During the LDN Stage The human ES cell or human iPS cell derived PE clusters are washed and further differentiated to endocrine progenitors (EP) and beta cell like cells (BC), using protocols for endocrine and beta cell induction, as described in WO2015/028614, WO2017/144695 and WO/2019/048690, which are all incorporated herein by reference in their entirety.

At the end of BC differentiation clusters were sampled, dissociated to single cells with TrypLE-Select (Gibco 12563-011), fixed in 10% formalin, stained with Cpep/Nkx6.1 and glucagon and analyzed by flow cytometry.

Figure 7A:
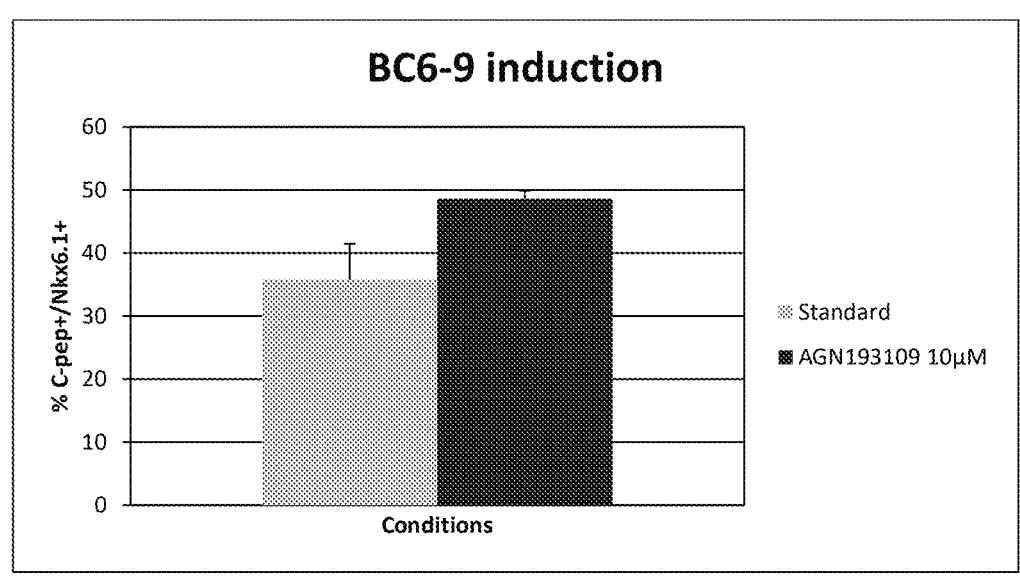
FIGS. 7A-B show the effect of AGN 193109 on PE2-3 on the induction of BC stage cells, evaluated by FACS analysis on day 6 to 9 of beta cell differentiation (BC6-9) on C-pep, Nkx6.1 and Glucagon expression.
Figure 7B:
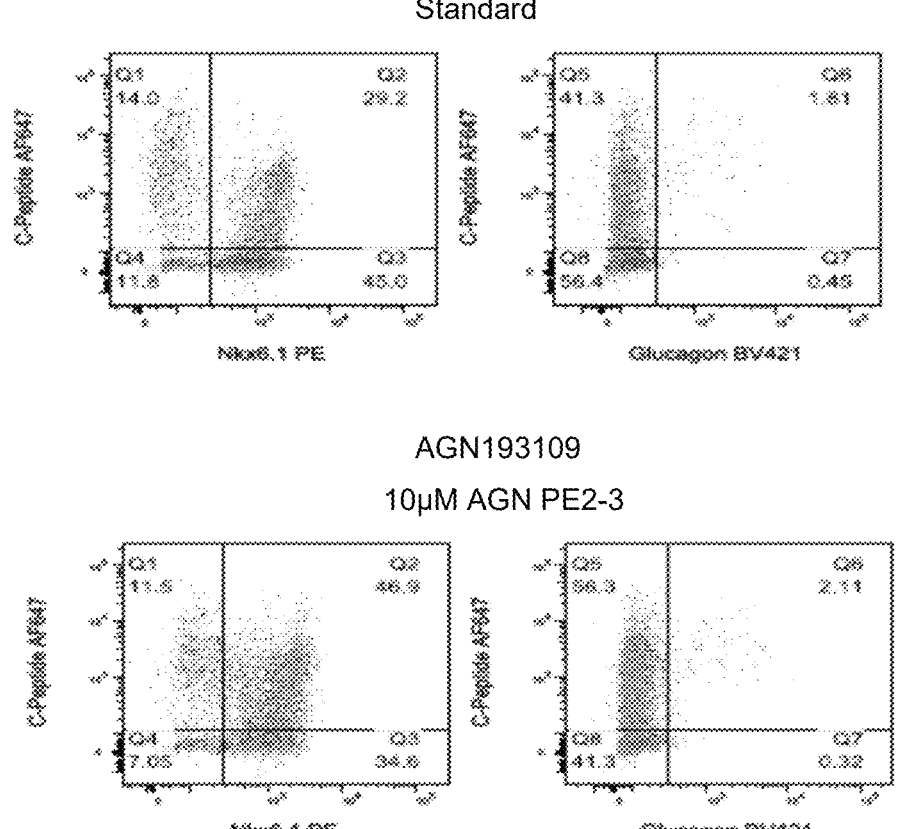

We observed a clear increase in the proportion of Cpep/Nkx6.1 double positive beta like cells after including AGN193109 in the LDN stage of the PE protocol, pointing to an improvement in the PE quality when using AGN193109. Cpep/Nkx6.1 double positive increased from around 35% to around 50% with the addition of AGN193109 (FIGS. 7A,B). This increase was not accompanied by an increase in Glucagon positive cells, pointing to a specific effect of AGN193109 on the PE competence to form beta like cells in later differentiation (FIG. 7B).

Figure 9:
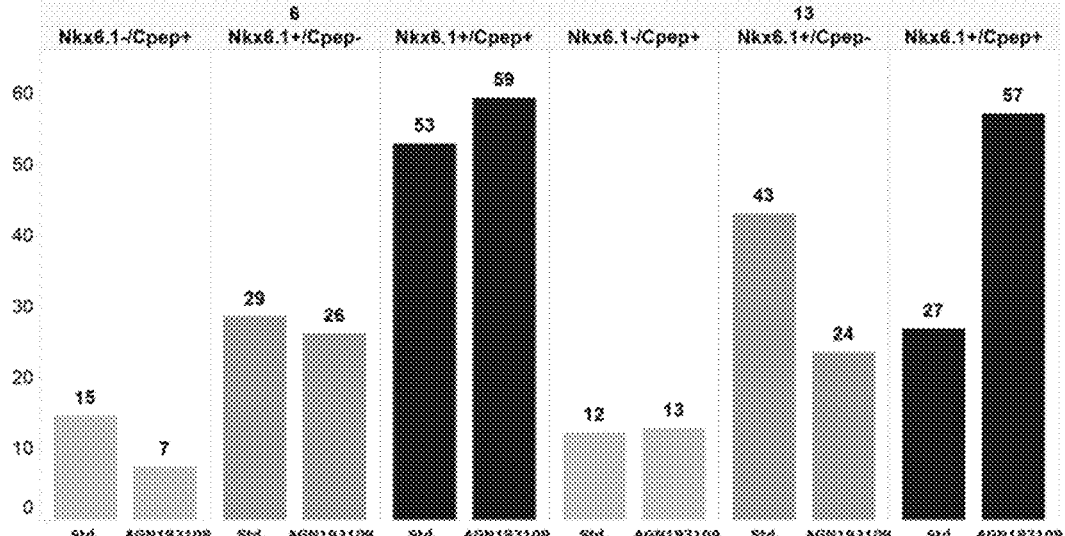
FIG. 9 shows the BC phenotype after cryopreservation and thawing on BC3, followed by prolonged culture on cells treated with the standard PE protocol or with AGN193109, evaluated by FACS analysis on C-pep/Nkx6.1 on BC6 and BC13.

In the context of cell therapy, a stable phenotype of the therapeutic cell type is a significant advantage as it allows for transportation and storage of the cell product prior to transplantation to patients. With the addition of AGN193109 during PE induction, we observed an improved stability of the beta cell phenotype with extended in vitro culture. In experiments with near identical phenotype on day 6 of BC differentiation, for the standard protocol we observed a dramatic decrease 1 week later on BC day 13. The standard protocol decreased from 53% to 27% Cpep/Nkx6.1 double positive, whereas the AGN193109 protocol only had a very minor decrease from 59% to 57% double positive from BC day 6 to BC day 13 (FIG. 9A).

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A method of differentiating definitive endoderm (DE) cells derived from human pluripotent stem cells into pancreatic endoderm (PE) cells, comprising, culturing the DE cells in a culture medium comprising a retinoic acid receptor (RAR) antagonist to produce pancreatic endoderm precursor cells, and culturing the pancreatic endoderm precursor cells in a cell culture medium comprising a RAR agonist to produce the PE cells;

wherein the PE cells are PDX1+/NKX6.1+ double positive; wherein the RAR antagonist is AGN193109; wherein the RAR agonist is selected from the group consisting of AM580, All-trans retinoic acid, 9-cis retinoic acid, AC 261066, AC 55649, Adapalene, AM 80, BMS 753, BMS 961, CD 1530, CD 2314, CD 437, Ch 55, Isotretinoin, Tazarotene, TTNPB, and EC19; and wherein the concentration of the RAR antagonist is in a range of 0.5-100 μM.

2. The method according to claim 1, wherein the concentration of the RAR antagonist is in a range of 7-12 μM.

3. The method according to claim 1, wherein the culturing of the DE cells is performed for a duration in the range from one hour to six days.

4. The method according to claim 3, wherein the culturing of the DE cells is performed for a duration in the range from one hour to six days.

5. The method according to claim 1, wherein the RAR agonist is AM580.

6. The method according to claim 1, wherein the RAR antagonist is AGN 193109, the concentration of the RAR antagonist is in a range of 7-12 μM, the culturing of the DE cells is performed for a duration in the range from one hour to six days and wherein the RAR agonist is AM580.

7. A method for inducing pancreatic endoderm (PE) cells from human pluripotent stem cell-derived human definitive endoderm (DE) cells, which comprises:

a step of culturing the DE cells in a culture medium comprising a retinoic acid receptor (RAR) antagonist to obtain pancreatic endoderm precursor cells, followed by a step of culturing the pancreatic endoderm precursor cells in a cell culture medium comprising a RAR agonist, thereby inducing PE cells, wherein said PE cells are PDX-1+/NKX6.1+ double positive, wherein said RAR antagonist is AGN193109.

8. The method according to claim 7, wherein the concentration of said RAR antagonist is 0.5-100 μM.

9. The method according to claim 7, wherein said step of culturing the definitive endoderm cells in a culture medium comprising the RAR antagonist to obtain pancreatic endoderm precursor cells, has the duration of one hour to six days.

10. The method according to claim 9, wherein the duration is 1 to 4 days.

11. The method according to claim 10, wherein the duration is two days.

* * * * *